(12) United States Patent
Fischer et al.

(10) Patent No.: US 8,841,328 B2
(45) Date of Patent: Sep. 23, 2014

(54) SELECTIVE INSECTICIDES BASED ON ANTHRANILIC ACID DIAMIDES AND SAFENERS

(71) Applicants: Reiner Fischer, Monheim am Rhein (DE); Rüdiger Fischer, Pulheim (DE); Christian Funke, Leichlingen (DE); Achim Hense, Sulzbach (DE); Wolfram Andersch, Bergisch Gladbach (DE); Heike Hungenberg, Langenfeld (DE); Wolfgang Thielert, Odenthal (DE); Udo Reckmann, Köln (DE); Lothar Willms, Hofheim am Taunus (DE); Christian Arnold, Langenfeld (DE)

(72) Inventors: Reiner Fischer, Monheim am Rhein (DE); Rüdiger Fischer, Pulheim (DE); Christian Funke, Leichlingen (DE); Achim Hense, Sulzbach (DE); Wolfram Andersch, Bergisch Gladbach (DE); Heike Hungenberg, Langenfeld (DE); Wolfgang Thielert, Odenthal (DE); Udo Reckmann, Köln (DE); Lothar Willms, Hofheim am Taunus (DE); Christian Arnold, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 14/095,509

(22) Filed: Dec. 3, 2013

(65) Prior Publication Data

US 2014/0087946 A1 Mar. 27, 2014

Related U.S. Application Data

(60) Continuation of application No. 12/944,074, filed on Nov. 11, 2010, now Pat. No. 8,685,985, which is a division of application No. 11/572,362, filed as application No. PCT/EP2005/007791 on Jul. 18, 2005, now Pat. No. 8,017,632.

(30) Foreign Application Priority Data

Jul. 20, 2004 (DE) .......................... 10 2004 035 134

(51) Int. Cl.
| | |
|---|---|
| A01N 43/56 | (2006.01) |
| A01N 37/28 | (2006.01) |
| A01N 41/10 | (2006.01) |
| A01N 25/32 | (2006.01) |
| A01N 43/40 | (2006.01) |
| A01N 37/20 | (2006.01) |
| A01N 47/28 | (2006.01) |

(52) U.S. Cl.
CPC ................ *A01N 37/28* (2013.01); *A01N 41/10* (2013.01); *A01N 25/32* (2013.01); *A01N 43/40* (2013.01); *A01N 43/56* (2013.01); *A01N 37/20* (2013.01); *A01N 47/28* (2013.01)
USPC ........... 514/341; 514/340; 514/342; 514/336; 514/357; 514/616; 514/256; 514/311; 514/330

(58) Field of Classification Search
CPC ....... A01N 35/00; A01N 37/20; A01N 41/10; A01N 43/56
USPC ......... 514/341, 340, 342, 336, 357, 616, 256, 514/311, 330
See application file for complete search history.

(56) References Cited

U.S. PATENT DOCUMENTS 4,021,224 A 5/1977 Pallos et al.

FOREIGN PATENT DOCUMENTS

AU 3495189 11/1989

OTHER PUBLICATIONS

Bauer, T.A., et al., "Response of Selected Weed Species to Postemergence Imazethapyr and Bentazon," *Weed Tech.* 9:236-242, The Weed Science Society of America (1995).
(Continued)

*Primary Examiner* — Sean Basquill
(74) *Attorney, Agent, or Firm* — Sterne, Kessler, Goldstein & Fox P.L.L.C.

(57) ABSTRACT

The present invention relates to the use of selective insecticidal compositions, characterized by an effective amount of an active compound combination comprising
(a) (1) at least one haloalkylnicotinic acid derivative of the formula (I)

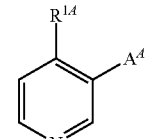

(I)

in which $A^A$ and $R^{1A}$ are as defined in the description,
or
(2) at least one phthalic acid diamide of the formula (II)

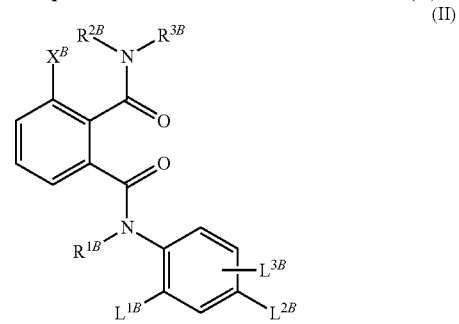

(II)

in which $X^B$, $R^{1B}$, $R^{2B}$, $R^{3B}$, $L^{1B}$, $L^{2B}$ and $L^{3B}$ are as defined in the description,
or
(3) at least one anthranilamide of the formula (III)

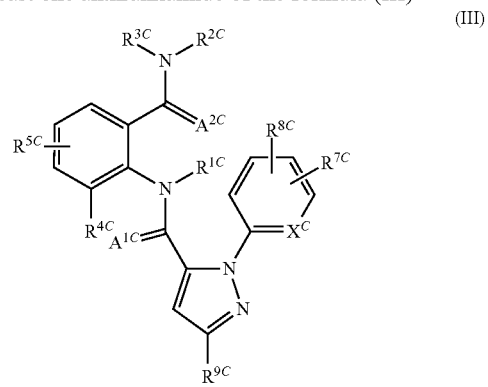

(III)

in which $A^{1C}$, $A^{2C}$, $X^C$, $R^{1C}$, $R^{2C}$, $R^{3C}$, $R^{4C}$, $R^{5C}$, $R^{7C}$, $R^{8C}$ and $R^{9C}$ are as defined in the description,
and
(b) at least one crop plant compatibility-improving compound from the group of compounds given in the description, in particular cloquintocet-mexyl, isoxadifen-ethyl and mefenpyr-diethyl
for controlling insects and/or arachnids, and a method for controlling insects and/or arachnids using the compositions.

6 Claims, No Drawings

(56) References Cited

U.S. PATENT DOCUMENTS

| | | | |
|---|---|---|---|
| 4,186,130 A | 1/1980 | Teach | |
| 4,623,727 A | 11/1986 | Hübele | |
| 4,639,266 A | 1/1987 | Heubach et al. | |
| 4,881,966 A | 11/1989 | Nyffeler et al. | |
| 4,891,057 A | 1/1990 | Sohn et al. | |
| 4,902,340 A | 2/1990 | Hubele | |
| 5,225,494 A | 7/1993 | Ishiga | |
| 5,314,863 A | 5/1994 | Löher et al. | |
| 5,380,852 A | 1/1995 | Schütze et al. | |
| 5,401,700 A | 3/1995 | Sohn et al. | |
| 5,516,750 A | 5/1996 | Willms et al. | |
| 5,700,758 A | 12/1997 | Rösch et al. | |
| 5,739,079 A | 4/1998 | Holdgrün et al. | |
| 6,235,680 B1 | 5/2001 | Ziemer et al. | |
| 6,251,827 B1 | 6/2001 | Ziemer et al. | |
| 6,555,501 B1 | 4/2003 | Bastiaans et al. | |
| 6,603,044 B1 | 8/2003 | Tohnishi et al. | |
| 6,642,379 B1 | 11/2003 | Furuya et al. | |
| 6,660,691 B2 | 12/2003 | Ziemer et al. | |
| 6,747,041 B1 | 6/2004 | Katsuhira et al. | |
| 6,864,289 B1 | 3/2005 | Tohnishi et al. | |
| 6,875,768 B1 | 4/2005 | Machiya et al. | |
| 7,135,499 B2 | 11/2006 | Konze et al. | |
| 7,288,572 B2 | 10/2007 | Konze et al. | |
| 7,361,653 B2 | 4/2008 | Sakata et al. | |
| 8,268,751 B2 * | 9/2012 | Funke et al. | 504/130 |
| 8,685,985 B2 | 4/2014 | Fischer et al. | |
| 2002/0010098 A1 | 1/2002 | Schaper et al. | |
| 2002/0013326 A1 | 1/2002 | Tiebes et al. | |
| 2002/0032328 A1 | 3/2002 | Shermolovich et al. | |
| 2002/0132813 A1 | 9/2002 | Schaper et al. | |
| 2003/0119852 A1 | 6/2003 | Beckmann et al. | |
| 2003/0162812 A1 | 8/2003 | Harmsen et al. | |
| 2003/0171220 A1 | 9/2003 | Ziemer et al. | |
| 2004/0006047 A1 | 1/2004 | Schaper et al. | |
| 2004/0009982 A1 | 1/2004 | Tohnishi et al. | |
| 2004/0077500 A1 | 4/2004 | Sakata et al. | |
| 2004/0077597 A1 | 4/2004 | Bretschneider et al. | |
| 2004/0097595 A1 | 5/2004 | Nakao et al. | |
| 2004/0116299 A1 | 6/2004 | Harayama et al. | |
| 2005/0004368 A1 | 1/2005 | Mio et al. | |
| 2007/0265266 A1 | 11/2007 | Fischer et al. | |
| 2008/0070803 A1 | 3/2008 | Egeland | |
| 2008/0319081 A1 | 12/2008 | Fischer et al. | |
| 2009/0012100 A1 | 1/2009 | Fischer et al. | |
| 2009/0093544 A1 | 4/2009 | Fischer et al. | |
| 2009/0118375 A1 | 5/2009 | Fischer et al. | |
| 2011/0059991 A1 * | 3/2011 | Fischer et al. | 514/256 |

FOREIGN PATENT DOCUMENTS

| | | | | |
|---|---|---|---|---|
| DE | WO99/16744 | * | 4/1999 | C07C 311/51 |
| EP | 0 312 763 A1 | | 4/1989 | |
| EP | 0 346 620 A1 | | 12/1989 | |
| EP | 0 580 374 B1 | | 1/1994 | |
| EP | 0 613 618 A1 | | 9/1994 | |
| EP | 0 580 374 B1 | | 1/1996 | |
| EP | 1 006 107 A2 | | 6/2000 | |
| EP | 1 006 107 A3 | | 6/2000 | |
| EP | 0 919 542 B1 | | 8/2006 | |
| JP | 7010841 A | | 1/1995 | |
| JP | 10101648 A | | 4/1998 | |
| JP | 10195072 A | | 7/1998 | |
| JP | 11180957 | | 7/1999 | |
| JP | 2001/335559 A | | 12/2001 | |
| JP | 2002/205991 A | | 7/2002 | |
| JP | 2003/113179 A | | 4/2003 | |
| JP | 2004/035439 A | | 2/2004 | |
| JP | 2004/083415 A | | 3/2004 | |
| WO | WO 99/59993 A1 | | 11/1999 | |
| WO | WO 01/09104 A1 | | 2/2001 | |
| WO | WO 01/14373 A1 | | 3/2001 | |
| WO | WO 01/70671 A2 | | 9/2001 | |
| WO | WO 01/70671 A3 | | 9/2001 | |
| WO | WO 02/34050 A1 | | 5/2002 | |
| WO | WO 02/094765 A2 | | 11/2002 | |
| WO | WO 02/094765 A3 | | 11/2002 | |
| WO | WO 02/094766 A1 | | 11/2002 | |
| WO | WO 02/094791 A1 | | 11/2002 | |
| WO | WO 03/015518 A1 | | 2/2003 | |
| WO | WO03/015519 | * | 2/2003 | A01N 43/56 |
| WO | WO 03/015519 A1 | | 2/2003 | |
| WO | WO 03/016282 A2 | | 2/2003 | |
| WO | WO 03/016282 A3 | | 2/2003 | |
| WO | WO 03/016283 A1 | | 2/2003 | |
| WO | WO 03/016284 A1 | | 2/2003 | |
| WO | WO 03/024222 A1 | | 3/2003 | |
| WO | WO 03/027099 A1 | | 4/2003 | |
| WO | WO 03/043990 A1 | | 5/2003 | |
| WO | WO 03/062226 A1 | | 7/2003 | |
| WO | WO 03/097604 A1 | | 11/2003 | |
| WO | WO 03/097605 A1 | | 11/2003 | |
| WO | WO2004/067528 | * | 8/2004 | C07D 401/04 |

OTHER PUBLICATIONS

Blackshaw, R.E., "HOE-39866 Use in Chemical Fallow Systems," Weed Tech. 3:420-428, The Weed Science Society of America (1989).

Blackshaw, R.E., "Synergistic Mixes of DPX-A7881 and Clopyralid in Canola (Brassica napus)," Weed Tech. 3:690-695, The Weed Science Society of America (1989).

Blackshaw, R.E., et al., "Herbicide Combinations for Postemergent Weed Control in Safflower (Carthamus tinctorius)," Weed Tech. 4:97-104, The Weed Science Society of America (1990).

Blouin, D.C., et al., "Analysis of Synergistic and Antagonistic Effects of Herbicides Using Nonlinear Mixed-Model Methodology," Weed Tech. 18:464-472, The Weed Science Society of America (2004).

Bradley, P.R., et al., "Response of Sorghum (Sorghum bicolor) to Atrazine, Ammonium Sulfate, and Glyphosate," Weed Tech. 14:15-18, The Weed Science Society of America (2000).

Buker, III, R.S., et al., "Confirmation and Control of a Paraquat-Tolerant Goosegrass (Eleusine indica) Biotype," Weed Tech. 16:309-313, The Weed Science Society of America (2002).

Burke, I.C., et al., "CGA-362622 Antagonizes Annual Grass Control with Clethodim," Weed Tech. 16:749-754, The Weed Science Society of America (2002).

Flint, J.L., et al., "Analyzing Herbicide Interactions, A Statistical Treatment of Colby's Method," Weed Tech. 2:304-309, The Weed Science Society of America (1988).

Gillespie, G.R., and Nalewaja, J.D., "Wheat (Triticum aestivum) Response to Triallate Plus Chlorsulfuron," Weed Tech. 3:20-23, The Weed Science Society of America (1989).

Green, J.M., et al., "Metribuzin and Chlorimuron Mixtures for Preemergence Broadleaf Weed Control in Soybeans, Glycine max," Weed Tech. 2:355-363, The Weed Science Society of America (1988).

Harker, K.N., and O'Sullivan, P.A., "Synergistic Mixtures of Sethoxydim and Fluazifop on Annual Grass Weeds," Weed Tech. 5:310-316, The Weed Science Society of America (1991).

Kent, L.M., et al., "Effect of Ammonium Sulfate, Imazapyr, and Environment on the Phytotoxicity of Imazethapyr," Weed Tech. 5:202-205, The Weed Science Society of America (1991).

Kotoula-Syka, E., et al., "Interactions between SAN 582H and Selected Safeners on Grain Sorghum (Sorghum bicolor) and Corn (Zea mays)," Weed Tech. 10:299-304, The Weed Science Society of America (1996).

Lanclos, D.Y., et al., "Glufosinate Tank-Mix Combinations in Glufosinate-Resistant Rice (Oryza sativa)," Weed Tech. 16:659-663, The Weed Science Society of America (2002).

Norris, J.L., et al., "Weed Control from Herbicide Combinations with Three Formulations of Glyphosate," Weed Tech. 15:552-558, The Weed Science Society of America (2001).

Novosel, K.M., et al., "Metolachlor Efficacy as Influenced by Three Acetolactate Synthase-Inhibiting Herbicides," Weed Tech. 12:248-253, The Weed Science Society of America (1998).

Palmer, E.W., et al., "Broadleaf Weed Control in Soybean (Glycine max) with CGA-277476 and Four Postemergence Herbicides," Weed Tech. 14:617-623, The Weed Science Society of America (2000).

Rummens, F.H.A., "An Improved Definition of Synergistic and Antagonistic Effects," Weed Science 23(1):4-6, The Weed Science Society of America, United States (1975).

(56) References Cited

OTHER PUBLICATIONS

Salzman, F.P., and Renner, K.A., "Response of Soybean to Combinations of Clomazone, Metribuzin, Linuron, Alachlor, and Atrazine," *Weed Tech.* 6:922-929, The Weed Science Society of America (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America (1998).

Shaw, D.R. and Arnold, J.C., "Weed Control from Herbicide Combinations with Glyphosate," *Weed Tech.* 16:1-6, The Weed Science Society of America (2002).

Snipes, C.E., and Allen, R.L., "Interaction of Graminicides Applied in Combination with Pyrithiobac," *Weed Tech.* 10:889-892, The Weed Science Society of America (1996).

Sun, Y.-P. & Johnson, E.R., "Analysis of Joint Action of Insecticides Against House Flies", *J. Econ. Entomol.* 53:887-892, United States (1960).

Tammes, P.M.L., "Isoboles, A Graphic Representation of Synergism in Pesticides," *Neth. J. Plant Path.* 70:73-80, Springer, Germany (1964).

Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America (1997).

Zhang, W., et al., "Fenoxaprop Interactions for Barnyardgrass (*Echinochloa crus-galli*) Control in Rice," *Weed Tech.* 19:293-297, The Weed Science Society of America (2005).

Office Action mailed Jan. 24, 2006, in U.S. Appl. No. 10/531,136, Jorg Konze et al., filed Sep. 21, 2005.

Office Action mailed Feb. 28, 2011, in U.S. Appl. No. 10/563,794, Reiner Fischer et al., filed Apr. 2, 2007.

Colby, S.R., "Calculating Synergistic and Antagonistic Responses of Herbicide Combinations," *Weeds* 15:20-22 (1967).

Keichersid, M.L., et al., "*Sorghum* (*Sorghum bicolor*) Seed Safeners at Insecticide Synergists," *Weed Sci.* 33:774-778, Weed Science Society of America (1985).

Database STN, Accession No. 134:143251, English language abstract for Morita, M., et al., "IKI-220-a novel systemic aphicide," *BCPC Conf. Pests & Diseases* 1:59-65, British Crop Protection Council (2000).

Database STN, Accession No. 138:182512, English language abstract for patent JP 2003/055115 A2.

Dialog File 351, Accession No. 4963457, English language abstract for EP 0 346 620 A.

Dialog File 351, Accession No. 7063122, English language abstract for JP 7010841 A.

Dialog File 351, Accession No. 8749606, English language abstract for JP 10101648 A.

Dialog File 351, Accession No. 8912535, English language abstract for JP 10195072 A.

Dialog File 351, Accession No. 9497027, English language abstract for JP 11180957 A.

Dialog File 351, Accession No. 9766183, English language abstract for WO 1999/059993.

Dialog File 351, Accession No. 11206003, English language abstract for JP 2001/335559 A.

Dialog File 351, Accession No. 12751378, English language abstract for JP 2002/205991 A.

Dialog File 351, Accession No. 13555034, English language abstract for JP 2003/113179 A.

Dialog File 351, Accession No. 14014647, English language abstract for JP 2004/035439 A.

Dialog File 351, Accession No. 14079036, English language abstract for JP 2004/083415 A.

International Search Report for International Application No. PCT/EP2005/007791, European Patent Office, Netherlands, mailed on Jun. 7, 2006.

Written Opinion of the International Searching Authority for International Application No. PCT/EP2005/007791, European Patent Office, Netherlands, issued on Jan. 23, 2007.

Office Action mailed Nov. 25, 2011, in U.S. Appl. No. 12/097,044 (now abandoned), inventors Funke et al., § 371(c) date Sep. 19, 2008.

Office Action mailed Jun. 28, 2011, in U.S. Appl. No. 12/097,044 (now abandoned), inventors Funke et al., § 371(c) date Sep. 19, 2008.

Office Action mailed Aug. 29, 2011, in U.S. Appl. No. 10/579,076 (now U.S. Patent No. 8,268,751), inventors Funke et al., § 371(c) date Sep. 28, 2007.

Office Action mailed Jul. 21, 2010, in U.S. Appl. No. 10/579,076 (now U.S. Patent No. 8,268,751), inventors Funke et al., § 371(c) date Sep. 28, 2007.

Office Action mailed Jan. 5, 2010, in U.S. Appl. No. 10/579,076 (now U.S. Patent No. 8,268,751), inventors Funke et al., § 371(c) date Sep. 28, 2007.

Office Action mailed Apr. 28, 2009, in U.S. Appl. No. 10/579,076 (now U.S. Patent No. 8,268,751), inventors Funke et al., § 371(c) date Sep. 28, 2007.

Office Action mailed Apr. 23, 2012, in U.S. Appl. No. 12/944,074, inventors Fischer, R., et al., filed Nov. 11, 2010.

Office Action mailed Sep. 6, 2012, in U.S. Appl. No. 12/944,074, inventors Fischer, R., et al., filed Nov. 11, 2010.

Gaillard, C., et al., "A herbicide antidote (safener) induces the activity of both the herbicide detoxifying enzyme and of a vacuolar transporter for the detoxified herbicide," *FEBS Let.* 352:219-221, Federation of European Biochemical Societies, Netherlands (1994).

Gressel, J., "Synergizing Pesticides to Reduce Use Rates," in *Pest Control with Enhanced Environmental Safety*, ACS Symposium Series, Duke, S., et al., eds., p. 48-61, American Chemical Society, United States (1993).

Hatzios, K.K., "Herbicide Safeners: Effective Inducers of Plant Defense Gene-Enzyme Systems," *Phytoparasitica* 31:3-7, Springer, Germany (2003).

\* cited by examiner

SELECTIVE INSECTICIDES BASED ON ANTHRANILIC ACID DIAMIDES AND SAFENERS

The invention relates to selective insecticidally and/or acaricidally effective compound combinations comprising, firstly, haloalkylnicotinic acid derivatives, phthalic acid diamides or anthranilic acid diamides and, secondly, at least one crop plant compatibility-improving compound, and to their use for the selective control of insects and/or spider mites in various crops of useful plants.

It is known that certain haloalkylnicotinic acid derivatives have insecticidal properties (EP-A 0 580 374, JP-A 7-010841, JP-A 7-025853, JP-A 10-101648, JP-A 10-195072, JP-A 11-180957, JP-A 2002-205991, JP-A 2003-113179, JP-A 2004-035439, JP-A 2004-083415, WO 98/57969, WO 99/59993, WO 00/35912, WO 00/35913, WO 01/09104, WO 01/14373, WO 01/47918, WO 01/70692, WO 02/12229, WO 03/028458, WO 03/028459, WO 03/043990, WO 03/044013, WO 03/097604, WO 03/097605).

Furthermore, it is known that certain anthranilic acid diamides have insecticidal properties (WO 01/70671, WO 02/094791, WO 03/015519, WO 03/016284, WO 03/015518, WO 03/024222, WO 03/016282, WO 03/016283, WO 03/062226, WO 03/027099).

Also known as compounds having insecticidal properties are phthalic acid diamides (cf. EP-A-0 919 542, EP-A-1 006 107, WO 01/00 575, WO 01/00 599, WO 01/46 124, JP-A 2001-33 555 9, WO 01/02354, WO 01/21 576, WO 02/08 8074, WO 02/08 8075, WO 02/09 4765, WO 02/09 4766, WO 02/06 2807).

The general formulae and definitions described in these publications and the individual compounds described therein are expressly incorporated herein by way of reference.

It is also known that mixtures of phthalic acid diamides and further bioactive compounds have an insecticidal and/or acaricidal action (WO 02/087 334). However, the activity of these mixtures is not always optimal.

Surprisingly, it has now been found that certain haloalkylnicotinic acid derivatives, phthalic acid diamides or anthranilic acid amides, when used together with the crop plant compatibility-improving compounds (safeners/antidotes) described below, are very efficient in preventing damage to the crop plants and can be used particularly advantageously as broadly active combination preparations for the selective control of insects.

The invention provides selective insecticidal and/or acaricidal compositions comprising an effective amount of an active compound combination comprising, as components, (a) (1) at least one haloalkylnicotinic acid derivative of the formula (I)

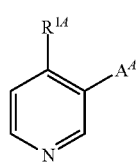

(I)

in which
$A^A$ represents one of the groups

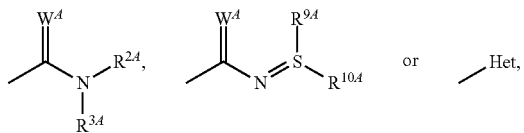

$R^{1A}$ represents $C_1$-$C_4$-haloalkyl,
$R^{2A}$ and $R^{3A}$ independently of one another represent hydrogen or hydroxyl,
represent $C_1$-$C_8$-alkyl, $C_3$-$C_6$-alkenyl, $C_3$-$C_6$-alkynyl, $C_1$-$C_6$-alkoxy, $C_3$-$C_8$-cycloalkyl or $C_3$-$C_8$-cycloalkyl-$C_1$-$C_6$-alkyl, each of which is optionally mono- or polysubstituted by identical or different substituents from the group consisting of $R^{4A}$, oximino and hydrazono, where the substituents oximino and hydrazono for their part are in each unsubstituted or may be substituted by $C_1$-$C_8$-alkyl, $C_3$-$C_6$-alkenyl, $C_3$-$C_6$-alkynyl, $C_3$-$C_8$-cycloalkyl, $C_3$-$C_8$-cycloalkyl-$C_1$-$C_6$-alkyl, $C_1$-$C_8$-alkoxy-$C_1$-$C_8$-alkyl, cyano-$C_1$-$C_8$-alkyl, $C_1$-$C_8$-alkylthio-$C_1$-$C_8$-alkyl, $C_1$-$C_8$-alkyl-carbonyl, ($C_1$-$C_8$-alkoxy)carbonyl, di-($C_1$-$C_8$-alkyl)aminocarbonyl, aryl or —$CH_2$-aryl
represent —C(=$X^A$)—$Y^A$, or represent aryl, heterocyclyl, —$CH_2$-aryl or —$CH_2$-heterocyclyl, each of which is optionally mono- or polysubstituted by identical or different substituents $R^{5A}$,
or
$R^{2A}$ and $R^{3A}$ together with the nitrogen atom to which they are attached form a 3- to 8-membered saturated, unsaturated or aromatic heterocyclic ring which optionally contains up to three further heteroatoms from the group consisting of nitrogen, sulfur and oxygen and which is unsubstituted or substituted by identical or different radicals from the group consisting of $R^{4A}$, $C_1$-$C_6$-alkyl, $C_1$-$C_6$-haloalkyl, $C_3$-$C_6$-alkenyl, $C_3$-$C_6$-alkynyl, oxo, oximino and hydrazono, where the substituents oximino and hydrazono for their part are unsubstituted or may be substituted by $C_1$-$C_8$-alkyl, $C_3$-$C_6$-alkenyl, $C_3$-$C_6$-alkynyl, $C_3$-$C_8$-cycloalkyl, $C_3$-$C_8$-cycloalkyl-$C_1$-$C_6$-alkyl, $C_1$-$C_8$-alkoxy-$C_1$-$C_8$-alkyl, cyano-$C_1$-$C_8$-alkyl, $C_1$-$C_8$-alkylthio-$C_1$-$C_8$-alkyl, $C_1$-$C_8$-alkyl-carbonyl, $C_1$-$C_8$-alkoxy-carbonyl, di-($C_1$-$C_8$-alkyl)aminocarbonyl, aryl or —$CH_2$-aryl,
$R^{4A}$ represents halogen, $C_1$-$C_6$-alkoxy, $C_1$-$C_6$-haloalkoxy, —S(O)$_n$—$C_1$-$C_6$-alkyl, —S(O)$_n$—$C_1$-$C_6$-haloalkyl, hydroxyl, cyano, carboxyl, azido, $C_1$-$C_6$-alkoxy-$C_1$-$C_6$-alkyl, $C_1$-$C_6$-alkylthio-$C_1$-$C_6$-alkyl, $C_1$-$C_6$-alkyl-carbonyl, $C_1$-$C_6$-alkoxy-carbonyl, nitro, di-($C_1$-$C_6$-alkyl)amino, or phenoxy which is optionally mono- or polysubstituted by identical or different substituents from the group consisting of $C_1$-$C_6$-alkyl, $C_1$-$C_6$-haloalkyl and halogen,
$R^{5A}$ represents $R^{4A}$, $C_1$-$C_6$-alkyl or $C_1$-$C_6$-haloalkyl,
$X^A$ represents oxygen or sulfur,
$Y^A$ represents $R^{6A}$, $OR^{6A}$, $SR^{6A}$, $NR^{7A}R^{8A}$,
$W^A$ represent oxygen or sulfur,
$R^{6A}$ represents $C_1$-$C_8$-alkyl, $C_3$-$C_8$-cycloalkyl or $C_3$-$C_8$-cycloalkyl-$C_1$-$C_6$-alkyl, each of which is optionally mono- or polysubstituted by identical or different substituents $R^{4A}$, or represents aryl, heterocyclyl, —$CH_2$-aryl or —$CH_2$-heterocyclyl, each of which is optionally mono- or polysubstituted by identical or different substituents $R^{5A}$, $R^{7A}$ represents hydroxyl, represents $C_1$-$C_8$-alkyl, $C_3$-$C_6$-alkenyl, $C_3$-$C_6$-alkynyl, $C_1$-$C_8$-alkoxy, hydroxy-$C_1$-$C_8$-alkyl, $C_3$-$C_6$-alkenyloxy, $C_3$-$C_6$-alkynyloxy, $C_3$-$C_8$-cycloalkyl, $C_3$-$C_8$-cycloalkyl-$C_1$-$C_6$-alkyl, —O—$CH_2$—$C_3$-$C_8$-cycloalkyl, each of which is optionally mono- or polysubstituted by identical or different substituents $R^{4A}$, represents aryl, heterocyclyl, aryloxy, heterocyclyloxy, —$CH_2$-aryl, —O—$CH_2$-aryl, —$CH_2$-heterocyclyl or —O—$CH_2$-heterocyclyl, each of which is optionally mono- or polysubstituted by identical or different substituents $R^{5A}$, $R^{8A}$ represents hydrogen, represents $C_1$-$C_8$-alkyl, $C_3$-$C_8$-cycloalkyl or $C_3$-$C_8$-cycloalkyl-$C_1$-$C_6$-alkyl, each of which is optionally mono- or polysubstituted by identical or different substituents $R^{4A}$, represents aryl, heterocyclyl, —$CH_2$-aryl or —$CH_2$-heterocyclyl, each of which is optionally mono- or polysubstituted by identical or different substituents $R^{5A}$, $R^{9A}$ and $R^{10A}$ independently of one another represent $C_1$-$C_8$-alkyl, $C_3$-$C_6$-alkenyl, $C_3$-$C_6$-alkynyl, $C_3$-$C_8$-cycloalkyl or $C_3$-$C_8$-cycloalkyl-$C_1$-$C_6$-alkyl, each of which is optionally mono- or polysubstituted by identical or different substituents $R^{4A}$, represent —C(=$X^A$)—$Y^A$, represent aryl, heterocyclyl, —$CH_2$-aryl or —$CH_2$-heterocyclyl, each of which is optionally mono- or polysubstituted by identical or different substituents $R^{5A}$, or $R^{9A}$ and $R^{10A}$ together with the sulfur atom to which they are attached a 3- to 8-membered saturated or unsaturated heterocyclic ring which optionally contains up to three further heteroatoms from the group consisting of nitrogen, sulfur and oxygen and which is unsubstituted or mono- or polysubstituted by identical or different radicals from the group consisting of $R^{4A}$, $C_1$-$C_6$-alkyl, $C_1$-$C_6$-haloalkyl, oxo, oximino and hydrazono, where the substituents oximino and hydrazono for their part are unsubstituted or may be substituted by $C_1$-$C_8$-alkyl, $C_3$-$C_6$-alkenyl, $C_3$-$C_6$-alkynyl, $C_3$-$C_8$-cycloalkyl, $C_3$-$C_8$-cycloalkyl-$C_1$-$C_6$-alkyl, $C_3$-$C_8$-alkoxy-$C_1$-$C_8$-alkyl, cyano-$C_1$-$C_8$-alkyl, $C_1$-$C_8$-alkylthio-$C_1$-$C_8$-alkyl, $C_1$-$C_8$-alkyl-carbonyl, $C_1$-$C_8$-alkoxy-carbonyl, di-($C_1$-$C_8$-alkyl)aminocarbonyl, aryl or —$CH_2$-aryl, Het represents a heterocyclic radical which contains one to two rings, which may be fully saturated, partially saturated or fully unsaturated or aromatic and which is interrupted by at least one or more identical or different atoms from the group consisting of nitrogen, sulfur and oxygen, where, however, two oxygen atoms must not be directly adjacent and at least one carbon atom must still be present in the ring, where the cyclic radical is unsubstituted or substituted by one or more radicals from the group consisting of $R^{4A}$, $C_1$-$C_6$-alkyl, $C_1$-$C_6$-haloalkyl, oxo, oximino and hydrazono, where the substituents oximino and hydrazono for their part are unsubstituted or may be substituted by $C_1$-$C_8$-alkyl, $C_3$-$C_6$-alkenyl, $C_3$-$C_6$-alkynyl, $C_3$-$C_8$-cycloalkyl, $C_3$-$C_8$-cycloalkyl-$C_1$-$C_6$-alkyl, $C_1$-$C_8$-alkoxy-$C_1$-$C_8$-alkyl, cyano-$C_1$-$C_8$-alkyl, $C_1$-$C_8$-alkylthio-$C_1$-$C_8$-alkyl, $C_1$-$C_8$-alkyl-carbonyl, $C_1$-$C_8$-alkoxy-carbonyl, di-($C_1$-$C_8$-alkyl)aminocarbonyl, aryl or —$CH_2$-aryl, or (2) at least one phthalic acid diamide of the formula (II)

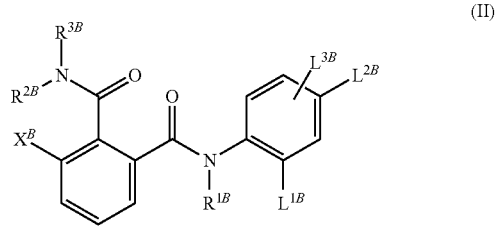

(II)

in which $X^B$ represents halogen, cyano, $C_1$-$C_8$-alkyl, $C_1$-$C_8$-haloalkyl, $C_1$-$C_8$-alkoxy or $C_1$-$C_8$-haloalkoxy, $R^{1B}$, $R^{2B}$ and $R^{3B}$ independently of one another represent hydrogen, cyano, represent optionally halogen-substituted $C_3$-$C_8$-cycloalkyl or represent the group -$M^{1B}$-$Q^B_k$, $M^{1B}$ represents optionally substituted $C_1$-$C_{12}$-alkylene, $C_3$-$C_{12}$-alkenylene or $C_3$-$C_{12}$-alkynylene, $Q^B$ represents hydrogen, halogen, cyano, nitro, $C_1$-$C_8$-haloalkyl, in each case optionally substituted $C_3$-$C_8$-cycloalkyl, $C_1$-$C_8$-alkyl-carbonyl or $C_1$-$C_8$-alkoxy-carbonyl, in each case optionally substituted phenyl, hetaryl or represents the group -$T^B$-$R^{4B}$, $T^B$ represents oxygen, —S(O)$_m$— or —N($R^{5B}$)—, $R^{4B}$ represents hydrogen, in each case optionally substituted $C_1$-$C_{12}$-alkyl, $C_3$-$C_{12}$-alkenyl, $C_3$-$C_{12}$-alkynyl, $C_3$-$C_3$-cycloalkyl, $C_3$-$C_8$-cycloalkyl-$C_1$-$C_6$-alkyl, $C_1$-$C_6$-alkoxy-$C_1$-$C_4$-alkyl, $C_1$-$C_8$-alkyl-carbonyl, $C_1$-$C_8$-alkoxy-carbonyl, phenyl, phenyl-$C_1$-$C_4$-alkyl, phenyl-$C_1$-$C_4$-alkoxy, hetaryl, hetaryl-$C_1$-$C_4$-alkyl, $R^{5B}$ represents hydrogen, represents in each case optionally substituted $C_1$-$C_8$-alkyl-carbonyl, $C_1$-$C_8$-alkoxy-carbonyl, phenyl-carbonyl or phenyl-$C_1$-$C_6$-alkoxy-carbonyl, k represents 1, 2, 3, or 4, m represents 0, 1 or 2, $R^{1B}$ and $R^{2B}$ together form an optionally substituted 4- to 7-membered ring, which may optionally be interrupted by heteroatoms, $L^{1B}$ and $L^{3B}$ independently of one another represent hydrogen, halogen, cyano or in each case optionally substituted $C_1$-$C_8$-alkyl, $C_1$-$C_8$-alkoxy, $C_1$-$C_6$-alkyl-S(O)$_m$—, phenyl, phenoxy or hetaryloxy, $L^{2B}$ represents hydrogen, halogen, cyano, in each case optionally substituted $C_1$-$C_{12}$-alkyl, $C_2$-$C_{12}$-alkenyl, $C_2$-$C_{12}$-alkynyl, $C_1$-$C_{12}$-haloalkyl, $C_3$-$C_8$-cycloalkyl, phenyl, hetaryl or represents the group -$M^{2B}$-$R^{6B}$, $M^{2B}$ represents oxygen or —S(O)$_m$—, $R^{6B}$ represents in each case optionally substituted $C_1$-$C_8$-alkyl, $C_2$-$C_8$-alkenyl, $C_3$-$C_6$-alkynyl $C_3$-$C_8$-cycloalkyl, phenyl or hetaryl, $L^{1B}$ and $L^{3B}$ or $L^{1B}$ and $L^{2B}$ in each case together form an optionally substituted 5- to 6-membered ring which may optionally be interrupted by heteroatoms, or (3) at least one anthranilamide of the formula (II)

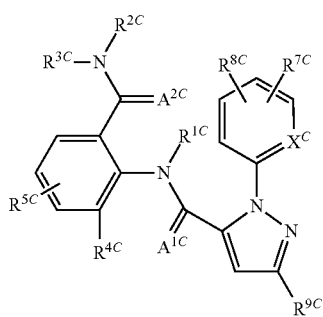

(III)

in which $A^{1C}$ and $A^{2C}$ independently of one another represent oxygen or sulfur, $X^C$ represents N or $CR^{10C}$, $R^{1C}$ represents hydrogen or represents $C_1$-$C_6$-alkyl, $C_2$-$C_6$-alkenyl, $C_2$-$C_6$-alkynyl or $C_3$-$C_6$-cycloalkyl, each of which may optionally be mono- or polysubstituted, where the substituents independently of one another may be selected from the group consisting of $R^{6C}$, halogen, cyano, nitro, hydroxyl, $C_1$-$C_4$-alkoxy, $C_1$-$C_4$-alkylthio, $C_1$-$C_4$-alkylsulfinyl, $C_1$-$C_4$-alkylsulfonyl, $C_2$-$C_4$-alkoxycarbonyl, $C_1$-$C_4$-alkylamino, $C_2$-$C_8$-dialkylamino, $C_3$-$C_6$-cycloalkylamino, ($C_1$-$C_4$-alkyl)$C_3$-$C_6$-cycloalkylamino and $R^{11C}$, $R^{2C}$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkylamino, $C_2$-$C_8$-dialkylamino, $C_3$-$C_6$-cycloalkylamino, $C_2$-$C_6$-alkoxycarbonyl or $C_2$-$C_6$-alkylcarbonyl, $R^{3C}$ represents hydrogen, $R^{11C}$ or represents $C_1$-$C_6$-alkyl, $C_2$-$C_6$-alkenyl, $C_2$-$C_6$-alkynyl, $C_3$-$C_6$-cycloalkyl, each of which is optionally mono- or polysubstituted, where the substituents independently of one another may be selected from the group consisting of $R^{6C}$, halogen, cyano, nitro, hydroxyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_2$-$C_6$-alkoxycarbonyl, $C_2$-$C_6$-alkylcarbonyl, $C_3$-$C_6$-trialkylsilyl, $R^{11C}$, phenyl, phenoxy and a 5- or 6-membered heteroaromatic ring, where each phenyl, phenoxy and 5- or 6-membered heteroaromatic ring may optionally be substituted and where the substituents independently of one another may be selected from one to three radicals $W^C$ or one or more radicals $R^{12C}$, or $R^{2C}$ and $R^{3C}$ may be attached to one another and form the ring $M^C$, $R^{4C}$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, nitro, hydroxyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, $C_2$-$C_8$-dialkylamino, $C_3$-$C_6$-cycloalkylamino, $C_3$-$C_6$-trialkylilyl or represents phenyl, benzyl or phenoxy, each of which may be mono- or polysubstituted, where the substituents independently of one another may be selected from the group consisting of $C_1$-$C_4$-alkyl, $C_2$-$C_4$-alkenyl, $C_2$-$C_4$-alkynyl, $C_3$-$C_6$-cyclalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, nitro, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylamino, $C_2$-$C_8$-dialkylamino, $C_3$-$C_6$-cycloalkylamino, ($C_1$-$C_6$-alkyl)($C_3$-$C_6$-cycloalkyl)amino, $C_2$-$C_4$-alkylcarbonyl, $C_2$-$C_6$-alkoxycarbonyl, $C_2$-$C_6$-alkyaminocarbonyl, $C_3$-$C_8$-dialkylaminocarbonyl and $C_3$-$C_6$-trialkylsilyl, $R^{5C}$ and $R^{8C}$ in each case independently of one another represent hydrogen, halogen or represent in each case optionally substituted $C_1$-$C_4$-alkyl, $C_1$-$C_4$-haloalkyl, $R^{12C}$, $G^C$, $J^C$, $-OJ^C$, $-OG^C$, $-S(O)_p$-$J^C$, $-S(O)_p$-$G^C$, $-S(O)_p$-phenyl, where the substituents independently of one another may be selected from one to three radicals W or from the group consisting of $R^{12C}$, $C_1$-$C_{10}$-alkyl, $C_2$-$C_6$-alkenyl, $C_2$-$C_6$-alkynyl, $C_1$-$C_4$-alkoxy and $C_1$-$C_4$-alkylthio, where each substituent may be substituted by one or more substituents independently of one another selected from the group consisting of $G^C$, $J^C$, $R^{6C}$, halogen, cyano, nitro, amino, hydroxyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, $C_2$-$C_8$-dialkylamino, $C_3$-$C_6$-trialkylsilyl, phenyl and phenoxy, where each phenyl or phenoxy ring may optionally be substituted and where the substituents independently of one another may be selected from one to three radicals W or one or more radicals $R^{12C}$, $G^C$ in each case independently of the others represents a 5- or 6-membered non-aromatic carbocyclic or heterocyclic ring which may optionally contain one or two ring members from the group consisting of C(=O), SO and S(=O)$_2$ and which may optionally be substituted by one to four substituents independently of one another selected from the group consisting of $C_1$-$C_2$-alkyl, halogen, cyano, nitro and $C_1$-$C_2$-alkoxy, or independently of the others represents $C_2$-$C_6$-alkenyl, $C_2$-$C_6$-alkynyl, $C_3$-$C_7$-cycloalkyl, (cyano)$C_3$-$C_7$-cycloalkyl, ($C_1$-$C_4$-alkyl)$C_3$-$C_6$-cycloalkyl, ($C_3$-$C_6$-cycloalkyl)$C_1$-$C_4$-alkyl, where each cycloalkyl, (alkyl)cycloalkyl and (cycloalkyl)alkyl may optionally be substituted by one or more halogen atoms, $J^C$ in each case independently of the others represents an optionally substituted 5- or 6-membered heteroaromatic ring, where the substituents independently of one another may be selected from one to three radicals $W^C$ or one or more radicals $R^{12C}$, $R^{6C}$ independently of the others represents $-C(=E^{1C})R^{19C}$, $-L^C C(=E^{1C})R^{19C}$, $-C(=E^{1C})L^C R^{19C}$, $-L^C C(=E^{1C})L^C R^{19}$, $-OP(=Q^C)(OR^{19C})_2$, $-SO_2 L^C R^{18C}$ or $-L^C SO_2 L^C R^{19C}$, where each $E^{1C}$ independently of the others represents O, S, N—$R^{15C}$, N—$OR^{15C}$, N—N($R^{15C}$), N—S=O, N—CN or N—NO$_2$, $R^{7C}$ represents hydrogen, $C_1$-$C_4$-alkyl, $C_1$-$C_4$-haloalkyl, halogen, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfnyl, $C_1$-$C_4$-haloalkylsulfonyl, $R^{9C}$ represents $C_1$-$C_4$-haloalkyl, $C_1$-$C_4$-haloalkoxy, $C_1$-$C_4$-haloalkylsulfinyl or halogen, $R^{10C}$ represents hydrogen, $C_1$-$C_4$-alkyl, $C_1$-$C_4$-haloalkyl, halogen, cyano or $C_1$-$C_4$-haloalkoxy, $R^{11C}$ in each case independently of the others represents in each case optionally mono- to trisubstituted $C_1$-$C_6$-alkylthio, $C_1$-$C_6$-alkylsulfenyl, $C_1$-$C_6$-haloalkylthio, $C_1$-$C_6$-haloalkylsulfenyl, phenylthio or phenylsulfenyl, where the substituents independently of one another may be selected from the group consisting of $W^C$, —S(O)$_n$N(R$^{16C}$)$_2$, —C(=O)R$^{13C}$, -L$^C$(C=O)R$^{14C}$, —S(C=O)L$^C$R$^{14C}$, —C(=O)L$^C$R$^{13C}$, —S(O)$_n$NR$^{13C}$C(=O)R$^{13C}$, —S(O)$_n$NR$^{13C}$C(=O)L$^C$R$^{14C}$ and —S(O)$_n$NR$^{13C}$S(O)$_2$L$^C$R$^{14C}$, $L^C$ in each case independently of the others represents O, NR$^{18C}$ or S, $R^{12}$ in each case independently of the others represents —B(OR$^{17C}$)$_2$, amino, SH, thiocyanato, $C_3$-$C_8$-trialkylsilyloxy, $C_1$-$C_4$-alkyl disulfide, —SF$_5$, —C(=E$^{1C}$)R$^{19C}$, -L$^C$C(=E$^{1C}$)R$^{19C}$, —C(=E$^{1C}$)L$^C$R$^{19C}$, -L$^C$C(=E$^{1C}$)L$^C$R$^{19C}$, —OP(=Q$^C$)(OR$^{19C}$)$_2$, —SO$_2$L$^C$R$^{19C}$ or -L$^C$SO$_2$L$^C$R$^{19C}$, $Q^C$ represents O or S, $R^{13C}$ in each case independently of the others represents hydrogen or represents in each case optionally mono- or polysubstituted $C_1$-$C_6$-alkyl, $C_2$-$C_6$-alkenyl, $C_2$-$C_6$-alkynyl or $C_3$-$C_6$-cycloalkyl, where the substituents independently of one another may be selected from the group consisting of R$^{6C}$, halogen, cyano, nitro, hydroxyl, $C_1$-$C_4$-alkoxy, $C_1$-$C_4$-alkylsulfinyl, $C_1$-$C_4$-alkylsulfonyl, $C_1$-$C_4$-alkylamino, $C_2$-$C_8$-dialkylamino, $C_3$-$C_6$-cycloalkylamino and ($C_1$-$C_4$-alkyl)$C_3$-$C_6$-cycloalkylamino, $R^{14C}$ in each case independently of the others represents in each case optionally mono- or polysubstituted $C_1$-$C_{20}$-alkyl, $C_2$-$C_{20}$-alkenyl, $C_2$-$C_{20}$-alkynyl or $C_3$-$C_6$-cycloalkyl, where the substituents independently of one another may be selected from the group consisting of R$^6$, halogen, cyano, nitro, hydroxyl, $C_1$-$C_4$-alkoxy, $C_1$-$C_4$-alkylsulfinyl, $C_1$-$C_4$-alkylsulfonyl, $C_1$-$C_4$-alkylamino, $C_2$-$C_8$-dialkylamino, $C_3$-$C_6$-cycloalkylamino and ($C_1$-$C_4$-alkyl)$C_3$-$C_6$-cycloalkylamino or represents in each case optionally substituted phenyl, where the substituents independently of one another may be selected from one to three radicals $W^C$ or one or more radicals R$^{12C}$, $R^{15C}$ in each case independently of one another of the others represents hydrogen or represents in each case optionally mono- or polysubstituted $C_1$-$C_6$-haloalkyl or $C_1$-$C_6$-alkyl, where the substituents independently of one another may be selected from the group consisting of cyano, nitro, hydroxyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, $C_2$-$C_8$-dialkylamino, $C_2$-$C_6$-alkoxycarbonyl, $C_2$-$C_6$-alkylcarbonyl, $C_3$-$C_6$-trialkylsilyl and optionally substituted phenyl, where the substituents independently of one another may be selected from one to three radicals W or one or more radicals R$^{12C}$, or N(R$^{15C}$)$_2$ represents a cycle which forms the ring M$^C$, $R^{16C}$ represents $C_1$-$C_{12}$-alkyl or $C_1$-$C_{12}$-haloalkyl, or N(R$^{16C}$)$_2$ represents a cycle which forms the ring M$^C$, $R^{17C}$ in each case independently of the others represents hydrogen or $C_1$-$C_4$-alkyl, or B(OR$^{17C}$)$_2$ represents a ring in which the two oxygen atoms are attached via a chain to two to three carbon atoms, which are optionally substituted by one or two substituents independently of one another selected from the group consisting of methyl and $C_2$-$C_6$-alkoxycarbonyl, $R^{18C}$ in each case independently of the others represents hydrogen, $C_1$-$C_6$-alkyl or $C_1$-$C_6$-haloalkyl, or N(R$^{13C}$)(R$^{18C}$) represents a cycle which forms the ring M$^C$, $R^{19C}$ in each case independently of the others represents hydrogen or represents in each case optionally mono- or polysubstituted $C_1$-$C_6$-alkyl, where the substitutents independently of one another may be selected from the group consisting of cyano, nitro, hydroxyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, $C_2$-$C_8$-dialkylamino, CO$_2$H, $C_2$-$C_6$-alkoxycarbonyl, $C_2$-$C_6$-alkylcarbonyl, $C_3$-$C_6$-trialkylsilyl and optionally substituted phenyl, where the substituents independently of one another may be selected from one to three radicals $W^C$, $C_1$-$C_6$-haloalkyl, $C_3$-$C_6$-cycloalkyl or phenyl or pyridyl, each of which is optionally mono- to trisubstituted by $W^C$, $M^C$ in each case represents an optionally mono- to tetrasubstituted ring which, in addition to the nitrogen atom attached to the substituent pair R$^{13C}$ and R$^{18C}$, (R$^{15C}$)$_2$ or (R$^{16C}$)$_2$ contains two to six carbon atoms and optionally additionally a further nitrogen, sulfur or oxygen atom, where the substituents independently of one another may be selected from the group consisting of $C_1$-$C_2$-alkyl, halogen, cyano, nitro and $C_1$-$C_2$-alkoxy, $W^C$ in each case independently of the others represents $C_1$-$C_4$-alkyl, $C_2$-$C_4$-alkenyl, $C_2$-$C_4$-alkynyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, nitro, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylamino, $C_2$-$C_8$-dialkylamino, $C_3$-$C_6$-cycloalkylamino, ($C_1$-$C_4$-alkyl)$C_3$-$C_6$-cycloalkylamino, $C_2$-$C_4$-alkylcarbonyl, $C_2$-$C_6$-alkoxycarbonyl, CO$_2$H, $C_2$-$C_6$-alkylaminocarbonyl, $C_3$-$C_8$-dialkylaminocarbonyl or $C_3$-$C_6$-trialkylsilyl, n represents 0 or 1, p represents 0, 1 or 2, where if (a) R$^{5C}$ represents hydrogen, $C_1$-$C_6$-alkyl, $C_1$-$C_6$-haloalkyl, $C_2$-$C_6$-haloalkenyl, $C_2$-$C_6$-haloalkynyl, $C_1$-$C_4$-haloalkoxy, $C_1$-$C_4$-haloalkylthio or halogen and (b) R$^{8C}$ represents hydrogen, $C_1$-$C_6$-alkyl, $C_1$-$C_6$-haloalkyl, $C_2$-$C_6$-haloalkenyl, $C_2$-$C_6$-haloalkynyl, $C_1$-$C_4$-haloalkoxy, $C_1$-$C_4$-haloalkylthio, halogen, $C_2$-$C_4$-alkylcarbonyl, $C_2$-$C_6$-alkoxycarbonyl, $C_2$-$C_6$-alkylaminocarbonyl or $C_3$-$C_8$-dialkylaminocarbonyl, (c) at least one substituent selected from the group consisting of R$^{6C}$, R$^{11C}$ and R$^{12C}$ is present and (d) if R$^{12C}$ is not present, at least one R$^{6C}$ or R$^{11C}$ is different from $C_2$-$C_6$-alkylcarbonyl, $C_2$-$C_6$-alkoxycarbonyl, $C_2$-$C_6$-alkylaminocarbonyl and $C_3$-$C_8$-dialkylaminocarbonyl, and the compounds of the general formula (III) furthermore comprise N-Oxides and salts, and (b) at least one crop plant compatibility-improving compound from the following group of compounds:

4-dichloroacetyl-1-oxa-4-azaspiro[4.5]decane (AD-67, MON-4660), 1-dichloroacetyl-hexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinolin-8-oxy-acetate (cloquintocet-mexyl—cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolocarboxylate (isoxadifen-ethyl—cf. also related compounds in WO-A-95/07897), 1-(ethoxycarbonyl)ethyl-3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane 4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorphenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinolin-8-oxyacetate, 4-allyloxybutyl 5-chloroquinolin-8-oxyacetate, 1-allyloxyprop-2-yl 5-chloroquinolin-8-oxyacetate, methyl 5-chloroquinoxalin-8-oxyacetate, ethyl 5-chloroquinolin-8-oxyacetate, allyl 5-chloroquinoxalin-8-oxyacetate, 2-oxoprop-1-yl 5-chloroquinolin-8-oxyacetate, diethyl 5-chloroquinolin-8-oxymalonate, diallyl 5-chloroquinoxalin-8-oxymalonate, diethyl 5-chloroquinolin-8-oxymalonate (cf. also related compounds in EP-A-582 198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulfonylbenzene, 1-[4-(N-2-methoxybenzoylsulfamoyl)phenyl]-3-methylurea (alias N-(2-methoxybenzoyl)-4-[(methyl-aminocarbonyl)amino] benzenesulfonamide), 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthylsulfamoyl)phenyl]-3,3-dimethylurea, N-(2-methoxy-5-methylbenzoyl)-4-(cyclopropylaminocarbonyl)benzenesulfonamide, and/or one of the following compounds of the general formulae (IV-a), (IV-b), (IV-c)

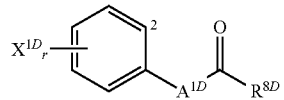
(IV-a)

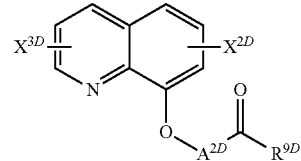
(IV-b)

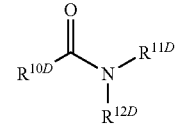
(IV-c)

where r represents 0, 1, 2, 3, 4 or 5, $A^{1D}$ represents one of the divalent heterocyclic groupings outlined below,

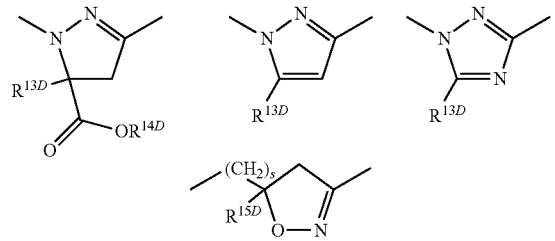

s represents 0, 1, 2, 3, 4 or 5, $A^{2D}$ represents optionally $C_1$-$C_4$-alkyl, $C_1$-$C_4$-alkoxy-carbonyl- and/or $C_1$-$C_4$-alkenyloxy-carbonyl-substituted $C_1$-$C_2$-alkanediyl, $R^{8D}$ represents hydroxyl, mercapto, amino, $C_1$-$C_6$-alkoxy, $C_1$-$C_6$-alkylthio, $C_1$-$C_6$-alkylamino or di-($C_1$-$C_6$-alkyl) amino, $R^{9D}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di-($C_1$-$C_4$-alkyl) amino, $R^{10D}$ represents in each case optionally fluorine-, chlorine- and/or bromine-substituted $C_1$-$C_4$-alkyl, $R^{11D}$ represents hydrogen, represents in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{12D}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{11D}$ and $R^{12D}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which together with the carbon atom to which they are attached form a 5- or 6-membered carbocycle, $R^{13D}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{14D}$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)silyl, $R^{15D}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^{1D}$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^{2D}$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^{3D}$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or one of the following compounds of the general formulae (IV-d), (IV-e)

(IV-d)

(IV-e)

where t represents 0, 1, 2, 3, 4 or 5, v represents 0, 1, 2, 3 or 4, $R^{16D}$ represents hydrogen or $C_1$-$C_4$-alkyl, $R^{17D}$ represents hydrogen or $C_1$-$C_4$-alkyl, $R^{18D}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di-($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{19D}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{20D}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{19D}$ represents in each case optionally $C_1$-$C_4$-alkyl-substituted $C_2$-$C_6$-alkanediyl or $C_2$-$C_5$-oxaalkanediyl, $X^{4D}$ represents nitro, cyano, carboxy, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^{5D}$ represents nitro, cyano, carboxy, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, for controlling insects and/or arachnids.

In the definitions above and below, the saturated or unsaturated hydrocarbon radicals, such as in alkyl, alkenyl or alkanediyl, are in each case straight-chain or branched—including in combination with heteroatoms, such as in alkoxy.

Unless indicated otherwise, optionally substituted radicals may be mono- or polysubstituted, where in the case of polysubstitution the substituents can be identical or different.

The definition $C_1$-$C_{20}$-alkyl comprises the largest range defined here for an alkyl radical. Specifically, this definition comprises the meanings methyl, ethyl, n-, isopropyl, n-, iso-, sec-, tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, and also in each case all isomeric hexyls (such as, for example, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl), heptyls (such as, for example, n-heptyl, 1-methylhexyl, 1-ethylpentyl, 2-ethylpentyl, 1-propylbutyl), octyls, nonyls, decyls, undecyls, dodecyls, tridecyls, tetradecyls, pentadecyles, hexadecyls, heptadecyls, octadecyls, nonadecyls and eicosyls.

These definitions may also be applied to alkyl radicals in combined meanings, such as, for example, in alkoxy, alkylamine, haloalkyl or cycloalkylalkyl. The extent of the definition is determined by the respective given range of carbon atoms.

The definition $C_2$-$C_{20}$-alkenyl comprises the largest range defined here for an alkenyl radical. Specifically, this definition comprises in particular the meanings vinyl, 1-propenyl, 2-propenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 2-ethyl-2-propenyl, 1-propyl-vinyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl- 4-pentenyl, 3-methyl-4-pentenyl, 4-methyl-4-pentenyl, 1,2-dimethyl-1-butenyl, 1,3-dimethyl-1-butenyl, 1,2-dimethyl-1-butenyl, 2,3-dimethyl-1-butenyl, 3,3-dimethyl-1-butenyl, 1-ethyl-1-butenyl, 2-ethyl-1-butenyl, 1,1-dimethyl-2-butenyl, 1,2-dimethyl-2-butenyl, 1,3-dimethyl-2-butenyl, 2,3-dimethyl-2-butenyl, 1-ethyl-2-butenyl, 2-ethyl-2-butenyl, 1,1-dimethyl-3-butenyl, 1,2-dimethyl-3-butenyl, 1,3-dimethyl-3-butenyl, 2,2-dimethyl-3-butenyl, 2,3-dimethyl-3-butenyl, 1-ethyl-3-butenyl, 2-ethyl-3-butenyl, 1,1,2-trimethyl-2-propenyl, 1-ethyl-1-methyl-2-propenyl, 1-ethyl-2-methyl-2-propenyl, and also in each case all isomeric heptenyls, octenyls, nonenyls, decenyls, undecenyls, dodecenyls, tridecenyls, tetradecenyls, pentadecenyls, hexadecenyls, heptadecenyls, octadecenyls, nonadecenyls and eicosenyls.

These definitions can also be applied to alkenyl radicals in combined meanings, such as, for example, in alkenyloxy or haloalkenyl. The extent of the definition is determined by the respective given range of carbon atoms.

The definition $C_2$-$C_{20}$-alkynyl comprises the largest range defined here for an alkynyl radical. Specifically, this definition comprises in particular the meanings ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 3,3-dimethyl-1-butynyl, 1,1-dimethyl-2-butynyl, 1-ethyl-2-butynyl, 1,1-dimethyl-3-butynyl, 1,2-dimethyl-3-butynyl, 2,2-dimethyl-3-butynyl, 1-ethyl-3-butynyl, 2-ethyl-3-butynyl, and also in each case all isomeric heptynyls, octynyls, nonynyls, decynyls, undecynyls, dodecynyls, tridecynyls, tetradecynyls, pentadecynyls, hexadecynyls, heptadecynyls, octadecynyls, nonadecynyls and eicosynyls.

These definitions may also be applied to alkynyl radicals in combined meanings, such as, for example, in alkynyloxy or haloalkynyl. The extent of the definition is determined by the respective given range of carbon atoms.

The definition $C_3$-$C_8$-cycloalkyl comprises the largest range defined here for a cycloalkyl radical. Specifically, this definition comprises the meanings cyclopropyl, cyclobutyl, cyclopentyl, cyclohexyl, cycloheptyl and cyclooctyl.

These definitions may also be applied to cycloalkyl radicals in combined meanings, such as, for example, in halocycloalkyl, cycloalkylamino or cycloalkylalkyl. The extent of the definition is determined by the respective given range of carbon atoms.

Oximino (hydroxyimino) represents a substituent =N—OH where the hydrogen atom may be replaced by the substituents given in each case.

Hydrazono represents a substituent =N—NH$_2$ where the two hydrogen atoms may each be replaced by the substituents given.

Aryl represents a mono- or polycyclic aromatic hydrocarbon radical, preferably a mono- to tricyclic radical having 6 to 14 carbon atoms, particularly preferably phenyl, naphthyl, anthracenyl or phenanthrenyl, very particularly preferably phenyl.

Heterocyclyl represents a mono- or bicyclic 3- to 10-membered radical which may be fully saturated, partially saturated or fully unsaturated or aromatic and which may be interrupted by at least one or more identical or different atoms from the group consisting of nitrogen, sulfur or oxygen, where, however, two oxygen atoms must not be directly adjacent and where at least one carbon atom must still be present in the ring. Heterocycles which may be mentioned are, in particular thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine, 4H-quinolizine, piperidine, pyrrolidine, oxazoline, tetrahydrofuran, tetrahydropyran, tetrahydrothiopyran, tetrahydrothiophene, isoxazolidine or thiazolidine.

Hetaryl or heteroaryl represents the substituted-group of definitions from heterocyclyl which is limited to the heteroaromatic ring systems.

Depending inter alia on the nature of the substituents, the compounds of the formula (I) may be present as geometrical and/or optical isomers or isomer mixtures of varying composition which, if appropriate, may be separated in a customary manner. Suitable for use in the compositions according to the invention and for the use according to the invention are both the pure isomers and the isomer mixtures. However, for the sake of simplicity, only compounds of the formula (I) are referred to, although what is meant are both the pure compounds and, if appropriate, also mixtures having varying proportions of isomeric compounds.

Including the individual meanings of $A^4$, the following principle structures (I-a), (I-b) and (I-c) result:

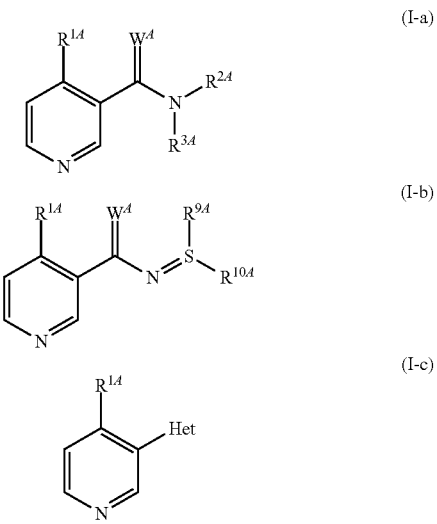

The formula (I) provides a general definition of the haloalkylnicotinic acid derivatives of the acaricidal and/or insecticidal compositions. Preferred substituents or ranges of the radicals listed in the formulae mentioned above and below are illustrated below:

$R^{1A}$ preferably represents $C_1$-$C_4$-alkyl which is mono- or polysubstituted by identical or different substituents from the group consisting of fluorine and chlorine, particularly preferably $CF_3$, $CHF_2$ or $CF_2Cl$, very particularly preferably $CF_3$;

$R^{2A}$ and $R^{3A}$ independently of one another preferably represent hydrogen or hydroxyl,
represent $C_1$-$C_6$-alkyl, $C_3$-$C_6$-alkenyl, $C_3$-$C_6$-alkynyl, $C_1$-$C_6$-alkoxy, $C_3$-$C_6$-cycloalkyl or $C_3$-$C_6$-cycloalkyl-$C_1$-$C_6$-alkyl, each of which is optionally mono- or polysubstituted by identical or different substituents from the group consisting of $R^{4A}$ and oximino, where the substituent oximino for its part is unsubstituted or may be substituted by $C_1$-$C_6$-alkyl, $C_3$-$C_6$-alkenyl, $C_3$-$C_6$-alkynyl, $C_3$-$C_6$-cycloalkyl, $C_3$-$C_6$-cycloalkyl-$C_1$-$C_4$-alkyl, $C_1$-$C_6$-alkoxy-$C_1$-$C_6$-alkyl, cyano-$C_1$-$C_6$-alkyl, $C_1$-$C_6$-alkylthio-$C_1$-$C_6$-alkyl, $C_1$-$C_6$-alkyl-carbonyl, $C_1$-$C_6$-alkoxy-carbonyl, di-($C_1$-$C_6$-alkyl)aminocarbonyl, aryl (in particular phenyl) or —$CH_2$-aryl (in particular benzyl), represent —$C(=X^A)$—$Y^A$, or represent aryl (in particular phenyl), heterocyclyl (in particular pyridinyl, pyrimidinyl, pyridazinyl, pyrazinyl, thiazolyl, isothiazolyl, oxazolyl, isoxazolyl, furyl, thienyl, pyrrolyl, pyrazolyl, thiadiazolyl, tetrahydropyranyl, tetrahydrothiopyranyl, tetrahydrofuryl, tetrahydrothienyl), —$CH_2$-aryl (in particular benzyl) or —$CH_2$-heterocyclyl (in particular —$CH_2$-pyridinyl, —$CH_2$-pyrimidinyl, —$CH_2$-pyridazinyl, —$CH_2$-pyrazinyl, —$CH_2$-thiazolyl, —$CH_2$-isothiazolyl, —$CH_2$-oxazolyl, —$CH_2$-isoxazolyl, furfuryl, thenyl, —$CH_2$-pyrrolyl, —$CH_2$-pyrazolyl, —$CH_2$-thiadiazolyl, —$CH_2$-tetrahydropyranyl, —$CH_2$-tetrahydrothiopyranyl, —$CH_2$-tetrahydrofuryl, —$CH_2$-tetrahydrothienyl), each of which is optionally mono- or polysubstituted by identical or different substituents $R^{5A}$,
or
$R^{2A}$ and $R^{3A}$ together with the nitrogen atom to which they are attached preferably form a 3- to 8-membered saturated, unsaturated or aromatic heterocyclic ring which optionally contains up to three further heteroatoms from the group consisting of nitrogen, sulfur and oxygen and which is unsubstituted or substituted by one or more radicals from the group consisting of $R^{4A}$, $C_1$-$C_6$-alkyl, $C_1$-$C_6$-haloalkyl and oximino, where the substituent oximino for its part is unsubstituted or may be substituted by $C_1$-$C_6$-alkyl, $C_3$-$C_6$-alkenyl, $C_3$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, cyano-$C_1$-$C_6$-alkyl, $C_1$-$C_6$-alkylthio-$C_1$-$C_6$-alkyl, $C_1$-$C_6$-alkyl-carbonyl, $C_1$-$C_6$-alkoxy-carbonyl, di-($C_1$-$C_6$-alkyl)aminocarbonyl, aryl (in particular phenyl) or —$CH_2$-aryl (in particular benzyl), $R^{4A}$ preferably represents halogen (particularly preferably fluorine, chlorine), $C_1$-$C_6$-alkoxy, $C_1$-$C_6$-haloalkoxy, —$S(O)_n$—$C_1$-$C_6$-alkyl, cyano, carboxyl, azido, $C_1$-$C_6$-alkoxy-$C_1$-$C_6$-alkyl, $C_1$-$C_6$-alkylthio-$C_1$-$C_6$-alkyl, $C_1$-$C_6$-alkyl-carbonyl, $C_1$-$C_6$-alkoxy-carbonyl, nitro or di-($C_1$-$C_6$-alkyl)amino, $R^{5A}$ preferably represents $R^{4A}$, $C_1$-$C_6$-alkyl or $C_1$-$C_6$-haloalkyl, $X^A$ preferably represents oxygen, $X^A$ furthermore preferably represents sulfur, $Y^A$ preferably represents $R^{6A}$, $OR^{6A}$, $SR^{6A}$, $NR^{7A}R^{8A}$, $W^A$ preferably represents oxygen, $W^A$ furthermore preferably represents sulfur, $R^{6A}$ preferably represents $C_1$-$C_6$-alkyl, $C_3$-$C_6$-cycloalkyl or $C_1$-$C_4$-cycloalkyl-$C_1$-$C_4$-alkyl, each of which is optionally mono- or polysubstituted by identical or different substituents $R^{4A}$, or represents aryl (in particular phenyl), heterocyclyl (in particular pyridinyl, thienyl, furyl), —$CH_2$-aryl (in particular benzyl) or —$CH_2$-heterocyclyl (in particular pyridinylmethyl, thenyl, furfuryl), each of which is optionally mono- or polysubstituted by identical or different substituents $R^{5A}$, $R^{7A}$ preferably represents hydroxyl, represents $C_1$-$C_6$-alkyl, $C_3$-$C_6$-alkenyl, $C_3$-$C_6$-alkynyl, $C_1$-$C_6$-alkoxy, hydroxy-$C_1$-$C_6$-alkyl, $C_3$-$C_6$-alkenyloxy, $C_3$-$C_6$-alkynyloxy, $C_3$-$C_6$-cycloalkyl, $C_3$-$C_6$-cycloalkyl-$C_1$-$C_6$-alkyl, —O—$CH_2$—$C_3$-$C_6$-cycloalkyl,
each of which is optionally mono- or polysubstituted by identical or different substituents $R^{4A}$, represents aryl (in particular phenyl), heterocyclyl (in particular pyridinyl, thienyl, furyl), aryloxy (in particular phenoxy), heterocyclyloxy (in particular pyridinyloxy, thienyloxy, furyloxy), —$CH_2$-aryl (in particular benzyl), —O—$CH_2$-aryl (in particular benzyloxy), —$CH_2$-heterocyclyl (in particular pyridinylmethyl, thenyl, furfuryl) or —O—$CH_2$-heterocyclyl (in particular pyridinylmethoxy, thenyloxy, furfuryloxy), each of which is optionally mono- or polysubstituted by identical or different substituents $R^{5A}$, $R^{8A}$ preferably represents hydrogen, represents $C_1$-$C_6$-alkyl, $C_3$-$C_6$-cycloalkyl or $C_3$-$C_6$-cycloalkyl-$C_1$-$C_4$-alkyl, each of which is optionally mono- or polysubstituted by identical or different substituents $R^{4A}$, represents aryl (in particular phenyl), heterocyclyl (in particular pyridinyl, thienyl, furyl), —$CH_2$-aryl (in particular benzyl) or —$CH_2$-heterocyclyl (in particular pyridinylmethyl, thenyl, furfuryl), each of which is optionally mono- or polysubstituted by identical or different substituents $R^{5A}$, $R^{9A}$ and $R^{10A}$ independently of one another preferably represent $C_1$-$C_8$-alkyl, $C_3$-$C_6$-alkenyl, $C_3$-$C_6$-alkynyl, $C_3$-$C_8$-cycloalkyl or $C_3$-$C_8$-cycloalkyl-$C_1$-$C_6$-alkyl, each of which is optionally mono- or polysubstituted by identical or different substituents $R^{4A}$, represent —$C(=X^A)$—$Y^A$, represent aryl (in particular phenyl), heterocyclyl (in particular pyridinyl, thienyl, furyl), —$CH_2$-aryl (in particular benzyl) or —$CH_2$-heterocyclyl (in particular pyridinylmethyl, thenyl, furfuryl), each of which is optionally mono- or polysubstituted by identical or different substituents $R^{5A}$,
or
$R^{9A}$ and $R^{10A}$ together with the sulfur atom to which they are attached preferably form a 3- to 8-membered saturated or unsaturated hetrocyclic ring which optionally contains up to three further heteroatoms from the group consisting of nitrogen, sulfur and oxygen, and which is unsubstituted or substituted by one or more radicals from the group consisting of $R^{4A}$, $C_1$-$C_6$-alkyl, $C_1$-$C_6$-haloalklyl, oxo, oximino and hydrazono, where the substituents oximino and hydrazono for their part are unsubstituted or may be substituted by $C_1$-$C_8$-alkyl, $C_3$-$C_6$-alkenyl, $C_3$-$C_6$-alkynyl, $C_3$-$C_8$-cycloalkyl, $C_3$-$C_8$-cycloalkyl-$C_1$-$C_6$-alkyl, $C_1$-$C_8$-alkoxy-$C_1$-$C_8$-alkyl, cyano-$C_1$-$C_8$-alkyl, $C_1$-$C_8$-alkylthio-$C_1$-$C_8$-alkyl, $C_1$-$C_8$-alkyl-carbonyl, $C_1$-$C_8$-alkoxy-carbonyl, di-($C_1$-$C_8$-alkyl)aminocarbonyl, aryl (in particular phenyl) or —$CH_2$-aryl (in particular benzyl), Het represents a heterocyclic radical from the group consisting of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazol, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine, 4H-quinolizine, piperidine, pyrrolidine, oxazoline, tetrahydrofuran, tetrahydropyran, isoxazolidine or thiazolidine, where the cyclic radical is unsubstituted or substituted by one or more radicals from the group consisting of $R^{4,4}$, $C_1$-$C_6$-alkyl, $C_1$-$C_6$-haloalkyl, oxo, oximino and hydrazono, where the substituents oximino and hydrazono for their part are unsubstituted or may be substituted by $C_1$-$C_8$-alkyl, $C_3$-$C_6$-alkenyl, $C_3$-$C_8$-alkynyl, $C_3$-$C_8$-cycloalkyl, $C_3$-$C_8$-cycloalkyl-$C_1$-$C_6$-alkyl, $C_1$-$C_8$-alkoxy-$C_1$-$C_8$-alkyl, cyano-$C_1$-$C_8$-alkyl, $C_1$-$C_8$-alkylthio-$C_1$-$C_8$-alkyl, $C_1$-$C_8$-alkyl-carbonyl, $C_1$-$C_8$-alkoxy-carbonyl, di-($C_1$-$C_8$-alkyl)aminocarbonyl, aryl (in particular phenyl) or —$CH_2$-aryl (in particular benzyl).

The general or preferred radical definitions or illustrations given above can be combined with another as desired, i.e. including combinations between the respective ranges and preferred ranges.

According to the invention, the insecticidal and/or acaricidal compositions preferably comprise compounds of the formula (I) which contain a combination of the meanings given above as being preferred (preferable).

According to the invention, the insecticidal and/or acaricidal compositions particularly preferably comprise compounds of the formula (I) which contain a combination of the meanings given above as being particularly preferred.

According to the invention, the insecticidal and/or acaricidal compositions very particularly preferably comprise compounds of the formula (I) which contain a combination of the meanings given above as being very particularly preferred.

Specifically, particular mention may be made of the following compounds of the formula (I-a):

TABLE 1

(I-a)

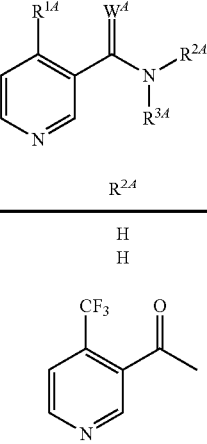

| No. | $R^{1A}$ | $W^A$ | $R^{2A}$ | $R^{3A}$ |
|---|---|---|---|---|
| I-a-1 | $CF_3$ | O | H | H |
| I-a-2 | $CF_3$ | O | H | $CH_2CN$ |
| I-a-3 | $CF_3$ | O | 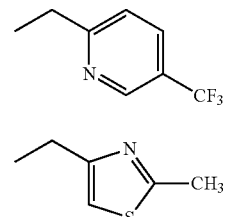 | $CH_2CN$ |
| I-a-4 | $CF_3$ | O | $CH_3$ | $CH_2CN$ |
| I-a-5 | $CF_3$ | O | $COCH_3$ | $CH_2CN$ |
| I-a-6 | $CF_3$ | O | H | 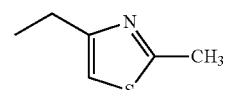 |
| I-a-7 | $CF_3$ | O | H | 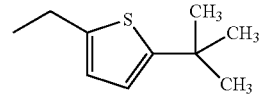 |
| I-a-8 | $CF_3$ | O | H | 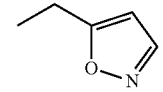 |
| I-a-9 | $CF_3$ | O | H | 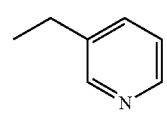 |
| I-a-10 | $CF_3$ | O | H |  |

TABLE 1-continued
(I-a)
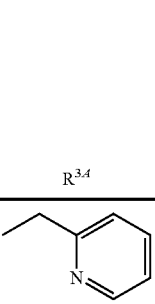
| No. | $R^{1A}$ | $W^A$ | $R^{2A}$ | $R^{3A}$ |
|---|---|---|---|---|
| I-a-11 | CF$_3$ | O | H | 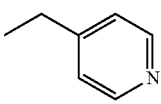 |
| I-a-12 | CF$_3$ | O | H | 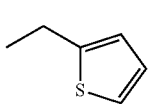 |
| I-a-13 | CF$_3$ | O | H | 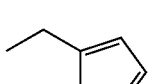 |
| I-a-14 | CF$_3$ | O | H | 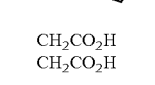 |
| I-a-15 | CF$_3$ | O | H | CH$_2$CO$_2$H |
| I-a-16 | CF$_3$ | O | CH$_2$CO$_2$H | CH$_2$CO$_2$H |
| I-a-17 | CF$_3$ | O | H | 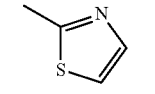 |
| I-a-18 | CF$_3$ | O | H | 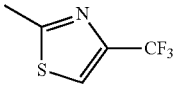 |
| I-a-19 | CF$_3$ | O | H | 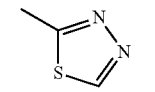 |
| I-a-20 | CF$_3$ | O | H | 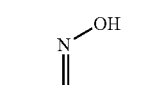 |
| I-a-21 | CF$_3$ | O | H | 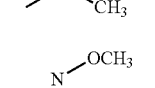 |
| I-a-22 | CF$_3$ | O | H | 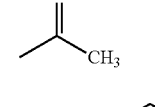 |
| I-a-23 | CF$_3$ | O | H | 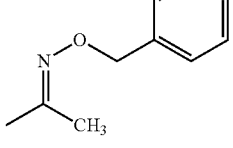 |

TABLE 1-continued (I-a)

| No. | R$^{1A}$ | W$^A$ | R$^{2A}$ | R$^{3A}$ |
|---|---|---|---|---|
| I-a-24 | CF$_3$ | O | H | –N=CH–CH$_3$ with N–OCH$_3$ (acetaldehyde O-methyloxime) |
| I-a-25 | CF$_3$ | O | CH$_3$ | OH |
| I-a-26 | CF$_3$ | O | CH$_3$ | OCH$_3$ |
| I-a-27 | CF$_3$ | O | 4-chlorophenyl | OCH$_3$ |
| I-a-28 | CF$_3$ | O | H | 4-tetrahydropyranyl (O) |
| I-a-29 | CF$_3$ | O | H | 4-tetrahydrothiopyranyl (S) |
| I-a-30 | CF$_3$ | O | H | 4-tetrahydrothiopyranyl S-oxide |
| I-a-31 | CF$_3$ | O | H | 4-tetrahydrothiopyranyl S,S-dioxide |
| I-a-32 | CF$_3$ | O | H | 2-methyl-3-tetrahydrofuranyl |
| I-a-33 | CF$_3$ | O | H | 3-tetrahydrothiophenyl S,S-dioxide |
| I-a-34 | CF$_3$ | O | H | 3-tetrahydrothiopyranyl S,S-dioxide |
| I-a-35 | CF$_3$ | O | Me | 3-tetrahydrothiophenyl S,S-dioxide |
| I-a-36 | CF$_3$ | O | —CH$_2$CH(N$_3$)CH$_2$— | |
| I-a-37 | CF$_3$ | O | —CH$_2$C(=N—OH)CH$_2$— | |
| I-a-38 | CF$_3$ | O | —CH$_2$C(=N—OCH$_3$)CH$_2$— | |

TABLE 1-continued (I-a)

| No. | R1A | WA | R2A | R3A |
|---|---|---|---|---|
| I-a-39 | CF3 | O | CH2OCH2CH3 | 5-methyl-3-methyl-isoxazol-4-yl |
| I-a-40 | CF3 | O | H | 5-methyl-isoxazol-3-yl |
| I-a-41 | CF3 | O | H | 5-methyl-3-ethyl-isoxazol-4-yl |
| I-a-42 | CF3 | O | H | 5-methyl-3-methyl-isoxazol-4-yl |
| I-a-43 | CF3 | O | CH2CN | 5-methyl-3-methyl-isoxazol-4-yl |
| I-a-44 | CF3 | O | H | 4,5-dimethyl-isoxazol-3-yl |
| I-a-45 | CF3 | O | H | CH3C(O)N(OCH3)(CH3) |
| I-a-46 | CF3 | O | H | (CH3)2CHN(OH)C(O)CH3 |
| I-a-47 | CF3 | O | H | CH3C(O)N(CH2Ph)(CH2CH2OH) |
| I-a-48 | CF3 | O | H | CH3C(O)NH-cyclopropyl |
| I-a-49 | CF3 | O | H | CH3C(O)NH-O-CH2Ph |

TABLE 1-continued
(I-a)
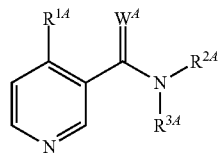
| No. | R$^{1A}$ | W$^A$ | R$^{2A}$ | R$^{3A}$ |
|---|---|---|---|---|
| I-a-50 | CF$_3$ | O | H | 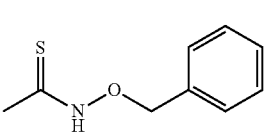 |
| I-a-51 | CF$_3$ | O | H | 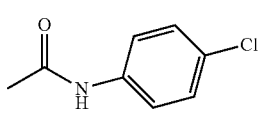 |
| I-a-52 | CF$_3$ | O | CH$_3$ | 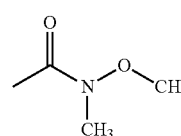 |
| I-a-53 | CF$_3$ | O | H | 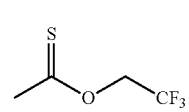 |
| I-a-54 | CF$_3$ | O | H | 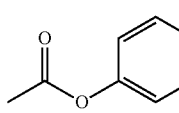 |
| I-a-55 | CF$_3$ | O | H | 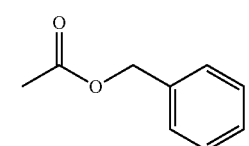 |
| I-a-56 | CF$_3$ | O | H | 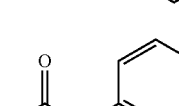 |
| I-a-57 | CF$_3$ | O | CH$_3$ | 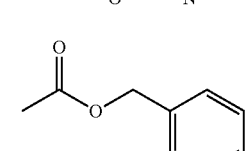 |
| I-a-58 | CF$_3$ | O | CH$_2$CN | 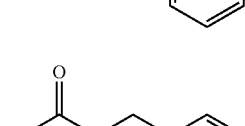 |
| I-a-59 | CF$_3$ | O | H | 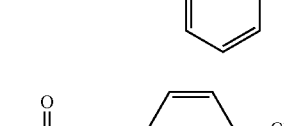 |

TABLE 1-continued (I-a)

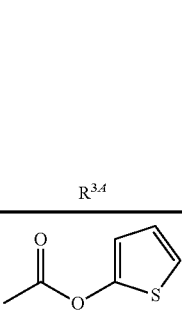

| No. | $R^{1A}$ | $W^A$ | $R^{2A}$ | $R^{3A}$ |
|---|---|---|---|---|
| I-a-60 | $CF_3$ | O | H | 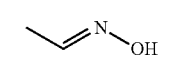 |
| I-a-61 | $CF_3$ | O | H | 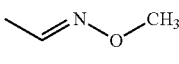 |
| I-a-62 | $CF_3$ | O | H | 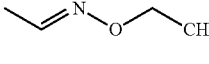 |
| I-a-63 | $CF_3$ | O | H | 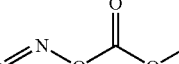 |
| I-a-64 | $CF_3$ | O | H | 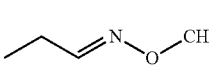 |
| I-a-65 | $CF_3$ | O | H | 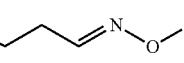 |
| I-a-66 | $CF_3$ | O | H | 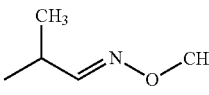 |
| I-a-67 | $CF_3$ | O | H | 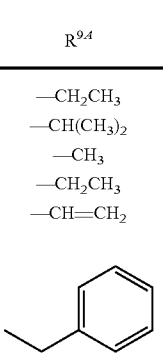 |

Specifically, particular mention may furthermore be made of the following compounds of the formula (I-b):

TABLE 2

(I-b)

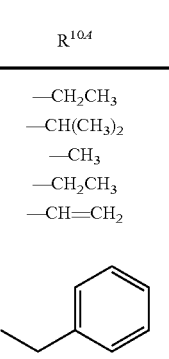

| No. | $R^{1A}$ | $W^A$ | $R^{9A}$ | $R^{10A}$ |
|---|---|---|---|---|
| I-b-1 | $CF_3$ | O | —$CH_2CH_3$ | —$CH_2CH_3$ |
| I-b-2 | $CF_3$ | O | —$CH(CH_3)_2$ | —$CH(CH_3)_2$ |
| I-b-3 | $CF_3$ | O | —$CH_3$ | —$CH_3$ |
| I-b-4 | $CF_3$ | O | —$CH_2CH_3$ | —$CH_2CH_3$ |
| I-b-5 | $CF_3$ | O | —CH=$CH_2$ | —CH=$CH_2$ |
| I-b-6 | $CF_3$ | O | benzyl | benzyl |
| I-b-7 | $CF_3$ | O | —$CH_3$ | —$CH_2CH_3$ |
| I-b-8 | $CF_3$ | O | —$CH_3$ | —$CH(CH_3)_2$ |
| I-b-9 | $CF_3$ | O | —$CH_3$ | phenyl |
| I-b-10 | $CF_3$ | O | —$CH_2CH_3$ | cyclohexyl |

Specifically, particular mention may furthermore be made of the following compounds of the formula (I-c):

TABLE 3

(I-c) structure: pyridine with R^(1A) and Het substituents

| No. | R^(1A) | Het |
|---|---|---|
| I-c-1 | $CF_3$ | 3-methyl-1,2,4-oxadiazol-5(4H)-one |
| I-c-2 | $CF_3$ | 3-methyl-N-(methoxycarbonyl)-1,2,4-oxadiazol-5(4H)-one with pivaloyl-like group (H3CO-C(=O)-N) |
| I-c-3 | $CF_3$ | 3-methyl-1,2,4-oxadiazole-5(4H)-thione |
| I-c-4 | $CF_3$ | 3-methyl-4-(2,2-dimethylpropanoyl)-1,2,4-oxadiazol-5(4H)-one |
| I-c-5 | $CF_3$ | 5-methyl-3-(1-methylethyl)-1,2,4-oxadiazole |
| I-c-6 | $CF_3$ | 2,5-dimethyl-1,3,4-oxadiazole |
| I-c-7 | $CF_3$ | 5-methyl-3-ethyl-1,2,4-oxadiazole |
| I-c-8 | $CF_3$ | 2-methyl-4-ethyl-4,5-dihydrooxazole |
| I-c-9 | $CF_3$ | 1,2,4-oxadiazole (5-substituted) |
| I-c-10 | $CF_3$ | 2,5-dimethyloxazole |
| I-c-11 | $CF_3$ | 2-methyl-5-(propylthiomethyl)oxazole |
| I-c-12 | $CF_3$ | 2-methyl-5-(methylthiomethyl)oxazole |
| I-c-13 | $CF_3$ | 5-methyl-3-(ethoxymethyl)-1,2,4-oxadiazole |
| I-c-14 | $CF_3$ | 6-methyl-3-methyl-1,3-oxazin-2(3H)-one |

Depending inter alia on the nature of the substituents, the compounds of the formula (I) may be present as geometrical and/or optical isomers or isomer mixtures of varying composition which, if appropriate, may be separated in a customary manner. Suitable for use in the compositions according to the invention and for the use according to the invention are both the pure isomers and the isomer mixtures. However, herein below, for the sake of simplicity, only compounds of the formula (II) are referred to, although what is meant are both the pure compounds and, if appropriate, also mixtures having varying proportions of isomeric compounds.

The formula (II) provides a general definition of the phthalic acid diamides of the acaricidal and/or insecticidal compositions. Preferred substituents and ranges of the radicals given in the formulae mentioned above and below are illustrated below:

$X^B$ preferably represents fluorine, chlorine, bromine, iodine, cyano, $C_1$-$C_6$-alkyl, $C_1$-$C_6$-haloalkyl, $C_1$-$C_6$-alkoxy or $C_1$-$C_6$-haloalkoxy, $R^{1B}$, $R^{2B}$ and $R^{3B}$ independently of one another preferably represent hydrogen, cyano, represent optionally halogen-substituted $C_3$-$C_6$-cycloalkyl or represent the group $M^{1B}$-$Q^B_k$, $M^{1B}$ preferably represents $C_1$-$C_8$-alkylene, $C_3$-$C_6$-alkenylene or $C_3$-$C_6$-alkynylene, $Q^B$ preferably represents hydrogen, halogen, cyano, nitro, $C_1$-$C_6$-haloalkyl or represents optionally fluorine-, chlorine-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulfur or represents in each optionally halogen-substituted $C_1$-$C_6$-alkyl-carbonyl or $C_1$-$C_6$-alkoxy-carbonyl or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano or nitro-substituted phenyl or hetaryl having 5 to 6 ring atoms (for example furanyl, pyridyl, imidazolyl, triazolyl, pyrazolyl, pyrimidyl, thiazolyl or thienyl) or represents the group -$T^B$-$R^{4B}$, $T^B$ preferably represents oxygen, —S(O)$_m$— or —N($R^{5B}$)—, $R^{4B}$ preferably represents hydrogen, represents in each case optionally fluorine- and/or chlorine-substituted $C_1$-$C_8$-alkyl, $C_3$-$C_8$-alkenyl, $C_3$-$C_8$-alkynyl, $C_3$-$C_8$-cycloalkyl, $C_3$-$C_8$-cycloalkyl-$C_1$-$C_2$-alkyl, $C_1$-$C_6$-alkyl-carbonyl, $C_1$-$C_6$-alkoxy-carbonyl, represents phenyl, phenyl-$C_1$-$C_4$-alkyl, phenyl-$C_1$-$C_4$-alkoxy, hetaryl or hetaryl-$C_1$-$C_4$-alkyl, each of which is mono- to tetrasubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, where hetaryl has 5 to 6 ring atoms (for example furanyl, pyridyl, imidazolyl, triazolyl, pyrazolyl, pyrimidyl, thiazolyl or thienyl), $R^{5B}$ preferably represents hydrogen, represents in each case optionally fluorine- and/or chlorine-substituted $C_1$-$C_6$-alkyl-carbonyl, $C_1$-$C_6$-alkoxy-carbonyl, represents phenyl-carbonyl or phenyl-$C_1$-$C_4$-alkyloxy-carbonyl, each of which is optionally mono- to tetrasubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, k preferably represents 1, 2 or 3, m preferably represents 0, 1 or 2, $R^{1B}$ and $R^{2B}$ together preferably form a 5- to 6-membered ring which may optionally be interrupted by an oxygen or sulfur atom, $L^{1B}$ and $L^{3B}$ independently of one another preferably represent hydrogen, cyano, fluorine, chlorine, bromine, iodine, $C_1$-$C_6$-alkyl, $C_1$-$C_4$-haloalkyl, $C_1$-$C_6$-alkoxy, $C_1$-$C_4$-haloalkoxy, $C_1$-$C_4$-alkyl-S(O)$_m$—, $C_1$-$C_4$-haloalkyl-S(O)$_m$—, represent phenyl, phenoxy, pyridinyloxy, thiazolyloxy or pyrimidinyloxy, each of which is mono- to trisubstituted by fluorine, chlorine, bromine, $C_1$-$C_6$-alkyl, $C_1$-$C_6$-alkoxy, $C_1$-$C_4$-haloalkyl, $C_1$-$C_4$-haloalkoxy, cyano or nitro, $L^{2B}$ preferably represents hydrogen, fluorine, chlorine, bromine, iodine, cyano, represents in each case optionally fluorine- and/or chlorine-substituted $C_1$-$C_{10}$-alkyl, $C_1$-$C_{10}$-alkenyl, $C_2$-$C_6$-alkynyl, represents in each case optionally fluorine-, chlorine-substituted $C_3$-$C_6$-cycloalkyl, represents phenyl, pyridinyl, thienyl, pyrimidyl or thiazolyl, each of which is optionally mono- to trisubstituted by fluorine, chlorine, bromine, $C_1$-$C_6$-alkyl, $C_1$-$C_6$-alkoxy, $C_1$-$C_4$-haloalkyl, $C_1$-$C_4$-haloalkoxy, cyano or nitro, or represents the group -$M^{2B}$-$R^{6B}$, $M^{2B}$ preferably represents oxygen or —S(O)$_m$—, $R^{6B}$ preferably represents in each case optionally fluorine- and/or chlorine-substituted $C_1$-$C_8$-alkyl, $C_2$-$C_8$-alkenyl, $C_3$-$C_6$-alkynyl or $C_3$-$C_6$-cycloalkyl, represents phenyl, pyridyl, pyrimidinyl or thiazolyl, each of which is optionally mono- to trisubstituted by fluorine, chlorine, bromine, $C_1$-$C_6$-alkyl, $C_1$-$C_6$-alkoxy, $C_1$-$C_4$-haloalkyl, $C_1$-$C_4$-haloalkoxy, cyano or nitro, $L^{1B}$ and $L^{3B}$ or $L^{1B}$ and $L^{2B}$ together each preferably form an optionally fluorine- and/or $C_1$-$C_2$-alkyl-substituted 5- to 6-membered ring which may optionally be interrupted by one or two oxygen atoms.

$X^B$ particularly preferably represents chlorine, bromine or iodine, $R^{1B}$, $R^{2B}$ and $R^{3B}$ independently of one another particularly preferably represent hydrogen or represent the group -$M^{1B}$-$Q^B_k$, $M^{1B}$ particularly preferably represents $C_1$-$C_8$-alkylene, $C_3$-$C_6$-alkenylene or $C_3$-$C_6$-alkynylene, $Q^B$ particularly preferably represents hydrogen, fluorine, chlorine, cyano, trifluoromethyl, $C_3$-$C_6$-cycloalkyl or represents the group -$T^B$-$R^{4B}$, $T^B$ particularly preferably represents oxygen or —S(O)$_m$—, $R^{4B}$ particularly preferably represents hydrogen, represents $C_1$-$C_6$-alkyl, $C_3$-$C_6$-alkenyl, $C_3$-$C_6$-alkynyl or $C_3$-$C_6$-cycloalkyl, each of which is optionally mono- to trisubstituted by fluorine and/or chlorine, k particularly preferably represents 1, 2 or 3, m particularly preferably represents 0, 1 or 2, $L^{1B}$ and $L^{3B}$ independently of one another particularly preferably represent hydrogen, fluorine, chlorine, bromine, iodine, cyano, $C_1$-$C_4$-alkyl, $C_1$-$C_2$-haloalkyl, $C_1$-$C_4$-alkoxy, $C_1$-$C_2$-haloalkoxy, represent phenyl or phenoxy, each of which is mono- to disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, cyano or nitro, $L^{2B}$ particularly preferably represents hydrogen, fluorine, chlorine, bromine, iodine, cyano, represents $C_1$-$C_6$-alkyl, $C_2$-$C_6$-alkenyl, $C_2$-$C_6$-alkynyl, $C_3$-$C_6$-cycloalkyl, each of which is optionally mono- to tridecasubstituted by fluorine and/or chlorine, or represents the group -$M^{2B}$-$R^{6B}$, $M^{2B}$ particularly preferably represents oxygen or —S(O)$_m$—, $R^{6B}$ particularly preferably represents $C_1$-$C_6$-alkyl, $C_2$-$C_6$-alkenyl, $C_2$-$C_6$-alkynyl or $C_3$-$C_6$-cycloalkyl, each of which is optionally mono- to tridecasubstituted by fluorine and/or chlorine, represents phenyl or pyridyl, each of which is optionally mono- to disubstituted by fluorine, chlorine, bromine, $C_1$-$C_4$-alkyl, $C_1$-$C_4$-alkoxy, trifluoromethyl, difluoromethoxy, trifluoromethoxy, cyano or nitro.

$X^B$ very particularly preferably represents iodine, $R^{1B}$ and $R^{2B}$ very particularly preferably represent hydrogen, $R^{3B}$ very particularly preferably represents the group -$M^{1B}$-$Q^B$, $M^{1B}$ very particularly preferably represents —CH(CH$_3$)CH$_2$—, —C(CH$_3$)$_2$CH$_2$—, —CH(C$_2$H$_5$)CH$_2$—, —C(CH$_3$)(C$_2$H$_5$)CH$_2$— or —C(C$_2$H$_5$)$_2$CH$_2$—, $Q^B$ very particularly preferably represents hydrogen, fluorine, chlorine, cyano, trifluoromethyl, $C_3$-$C_6$-cycloalkyl or represents the group -$T^B$-$R^{4B}$, $T^B$ very particularly preferably represents —S—, —SO— or —SO$_2$—, $R^{4B}$ very particularly preferably represents methyl, ethyl, n-propyl, isopropyl, n-butyl, isobutyl, sec-butyl or tert-butyl, allyl, butenyl or isoprenyl, each of which is optionally mono- to trisubstituted by fluorine and/or chlorine, $L^{1B}$ and $L^{3B}$ independently of one another very particularly preferably represent hydrogen, fluorine, chlorine, bromine, iodine, cyano, methyl, ethyl, n-propyl, iso-propyl, tert-butyl, methoxy, ethoxy, trifluoromethyl, difluoromethoxy or trifluoromethoxy, $L^{2B}$ very particularly preferably represents hydrogen, fluorine, chlorine, bromine, iodine, cyano, represents methyl, ethyl, n-propyl, isopropyl, n-butyl, isobutyl, sec-butyl, tert-butyl, allyl, butenyl or isoprenyl, each of which is optionally mono- to nonasubstituted by fluorine and/or chlorine, or represents the group -$M^{2B}$-$R^{6B}$, $M^{2B}$ very particularly preferably represents oxygen or sulfur, $R^{6B}$ very particularly preferably represents methyl, ethyl, n-propyl, isopropyl, n-butyl, isobutyl, sec-butyl, tert-butyl, allyl, butenyl or isoprenyl, each of which is optionally mono- to nonasubstituted by fluorine and/or chlorine, represents phenyl which is optionally mono- to disubstituted by fluorine, chlorine, bromine, methyl, ethyl, methoxy, trifluoromethyl, difluoromethoxy, trifluoromethoxy, cyano or nitro.

Specifically, particular mention may be made of the following compounds of the formula (II):

TABLE 4

(II)

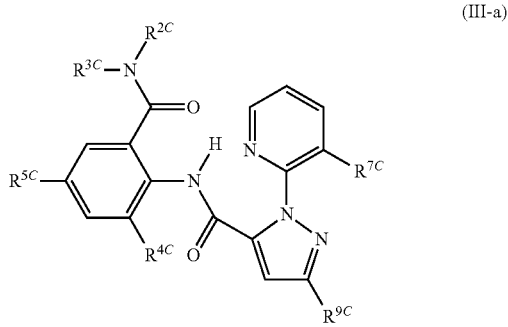

| No. | $X^B$ | $R^{1B}$ | $R^{2B}$ | $R^{3B}$ | $L^{1B}$ | $L^{2B}$ | $L^{3B}$ |
|---|---|---|---|---|---|---|---|
| II-1 | I | H | H | —C(CH$_3$)$_2$CH$_2$SCH$_3$ | CH$_3$ | iso-C$_3$F$_7$ | H |
| II-2 | I | H | H | —C(CH$_3$)$_2$CH$_2$SOCH$_3$ | CH$_3$ | iso-C$_3$F$_7$ | H |
| II-3 | I | H | H | —C(CH$_3$)$_2$CH$_2$SO$_2$CH$_3$ | CH$_3$ | iso-C$_3$F$_7$ | H |
| II-4 | I | H | H | —CH(CH$_3$)CH$_2$SCH$_3$ | CH$_3$ | iso-C$_3$F$_7$ | H |
| II-5 | I | H | H | —CH(CH$_3$)CH$_2$SOCH3 | CH$_3$ | iso-C$_3$F$_7$ | H |
| II-6 | I | H | H | —CH(CH$_3$)CH$_2$SO$_2$CH$_3$ | CH$_3$ | iso-C$_3$F$_7$ | H |

Depending inter alia on the nature of the substituents, the compounds of the formula (III) may be present as geometrical and/or optical isomers or isomer mixtures of varying composition which, if appropriate, may be separated in a customary manner. Suitable for use in the compositions according to the invention and for the use according to the invention are both the pure isomers and the isomer mixtures. However, herein below, for the sake of simplicity, only compounds of the formula (III) are referred to, although what is meant are both the pure compounds and, if appropriate, also mixtures having varying proportions of isomeric compounds.

The formula (II) provides a general definition of the anthranilamides of the acaricidal and/or insecticidal compositions. Preferred substituents or ranges of the radicals listed in the formulae given above and below are illustrated below:

Preference is given to active compound combinations comprising compounds of the formula (III-a)

(III-a)

in which
$R^{2C}$ represents hydrogen or $C_1$-$C_6$-alkyl,
$R^{3C}$ represents $C_1$-$C_6$-alkyl which is optionally substituted by a substituent $R^{6C}$,
$R^{4C}$ represents $C_1$-$C_4$-alkyl, $C_1$-$C_2$-haloalkyl, $C_1$-$C_2$-haloalkoxy or halogen,
$R^{5C}$ represents hydrogen, $C_1$-$C_4$-alkyl, $C_1$-$C_2$-haloalkyl, $C_1$-$C_2$-haloalkoxy or halogen,
$R^{6C}$ represents —C(=E$^{2C}$)R$^{19C}$, -L$^C$C(=E$^{2C}$)R$^{19C}$, —C(=E$^{2C}$)L$_C$R$^{19C}$ or -L$^C$C(=E$^{2C}$)L$^C$R$^{19C}$, where each E$^{2C}$ independently of the others represents O, S, N—R$^{15C}$, N—OR$^{15C}$, N—N(R$^{15C}$)$_2$ and each L$^C$ independently of the others represents O or NR$^{18C}$,
$R^{7C}$ represents $C_1$-$C_4$-haloalkyl or halogen,
$R^{8C}$ represents hydrogen,
$R^{9C}$ represents $C_1$-$C_2$-haloalkyl, $C_1$-$C_2$-haloalkoxy, S(O)$_p$C$_1$-$C_2$-haloalkyl or halogen,
$R^{15C}$ independently of the others represents hydrogen or represents in each case optionally substituted $C_1$-$C_6$-haloalkyl or $C_1$-$C_6$-alkyl, where the substituents independently of one another may be selected from the group consisting of cyano, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl or $C_1$-$C_4$-haloalkylsulfonyl,
$R^{18C}$ each represent hydrogen or $C_1$-$C_4$-alkyl,
$R^{19C}$ in each case independently of the others represents hydrogen or $C_1$-$C_6$-alkyl,
p independently of the others represents 0, 1, 2.

In the radical definitions mentioned as being preferred, halogen represents fluorine, chlorine, bromine and iodine, in particular fluorine, chlorine and bromine.

Particular preference is given to active compound combinations comprising compounds of the formula (II-a), in which
$R^{2C}$ represents hydrogen or methyl,
$R^{3C}$ represents $C_1$-$C_4$-alkyl,
$R^{4C}$ represents methyl, trifluoromethyl, trifluoromethoxy, fluorine, chlorine, bromine or iodine,
$R^{5C}$ represents hydrogen, fluorine, chlorine, bromine, iodine, trifluoromethyl or trifluoromethoxy,
$R^{7C}$ represents chlorine or bromine,
$R^{8C}$ represents hydrogen,
$R^{9C}$ represents trifluoromethyl, chlorine, bromine, difluoromethoxy or trifluoroethoxy.

Very particular preference is given to active compound combinations comprising the following compounds of the formula (III-a):

TABLE 5

(III-a)

| No. | $R^{2C}$ | $R^{3C}$ | $R^{4C}$ | $R^{5C}$ | $R^{7C}$ | $R^{9C}$ | m.p. (° C.) |
|---|---|---|---|---|---|---|---|
| III-a-1 | H | Me | Me | Cl | Cl | CF$_3$ | 185-186 |
| III-a-2 | H | Me | Me | Cl | Cl | OCH$_2$CF$_3$ | 207-208 |
| III-a-3 | H | Me | Me | Cl | Cl | Cl | 225-226 |
| III-a-4 | H | Me | Me | Cl | Cl | Br | 162-164 |
| III-a-5 | H | Me | Cl | Cl | Cl | CF$_3$ | 155-157 |
| III-a-6 | H | Me | Cl | Cl | Cl | OCH$_2$CF$_3$ | 192-195 |
| III-a-7 | H | Me | Cl | Cl | Cl | Cl | 205-206 |
| III-a-8 | H | Me | Cl | Cl | Cl | Br | 245-246 |
| III-a-9 | H | i-Pr | Me | Cl | Cl | CF$_3$ | 195-196 |
| III-a-10 | H | i-Pr | Me | Cl | Cl | OCH$_2$CF$_3$ | 217-218 |
| III-a-11 | H | i-Pr | Me | Cl | Cl | Cl | 173-175 |
| III-a-12 | H | i-Pr | Me | Cl | Cl | Br | 159-161 |
| III-a-13 | H | i-Pr | Cl | Cl | Cl | CF$_3$ | 200-201 |
| III-a-14 | H | i-Pr | Cl | Cl | Cl | OCH$_2$CF$_3$ | 232-235 |
| III-a-15 | H | i-Pr | Cl | Cl | Cl | Cl | 197-199 |

TABLE 5-continued

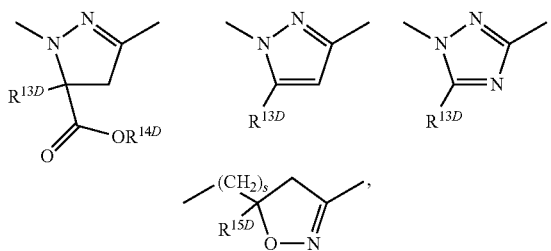

(III-a)

| No. | $R^{2C}$ | $R^{3C}$ | $R^{4C}$ | $R^{5C}$ | $R^{7C}$ | $R^{9C}$ | m.p. (° C.) |
|---|---|---|---|---|---|---|---|
| III-a-16 | H | i-Pr | Cl | Cl | Cl | Br | 188-190 |
| III-a-17 | H | Me | Me | CN | Cl | $CF_3$ | 214-216 |
| III-a-18 | H | Me | Me | CN | Cl | Br | 168-169 |

Depending inter alia on the nature of the substituents, the compounds of the formulae (IV-a), (IV-b), (IV-c), (IV-d) and (IV-e) may be present as geometrical and/or optical isomers or isomer mixtures of varying composition which, if appropriate, may be separated in a customary manner. Suitable for use in the compositions according to the invention and for the use according to the invention are both the pure isomers and the isomer mixtures. However, herein below, for the sake of simplicity, only compounds of the formulae (IV-a), (IV-b), (IV-c), (IV-d) and (IV-e) are referred to, although what is meant are both the pure compounds and, if appropriate, any mixtures having varying proportions of isomeric compounds.

Preferred meanings of the groups listed above in connection with the crop plant compatibility-improving compounds ("herbicide safeners") of the formulae (IV-a), (IV-b), (IV-c), (IV-d) and (IV-e) are defined below.

r preferably represents 0, 1, 2, 3 or 4, $A^{1D}$ preferably represents one of the divalent heterocyclic groupings outlined below s preferably represents 0, 1, 2, 3 or 4, $A^{2D}$ preferably represents in each case optionally methyl-, ethyl-, methoxycarbonyl-, ethoxycarbonyl- or allyloxycarbonyl-substituted methylene or ethylene, $R^{8D}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, $R^{9D}$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, $R^{10D}$ preferably represents in each case optionally fluorine-, chlorine- and/or bromine-substituted methyl, ethyl, n- or i-propyl, $R^{11D}$ preferably represents hydrogen, represents in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl, $R^{12D}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl, or together with $R^{11D}$ represents one of the radicals —$CH_2$—O—CH—$CH_2$ and —$CH_2$—$CH_2$—O—$CH_2$—$CH_2$— which are optionally substituted by methyl, ethyl, furyl, phenyl, a fused benzene ring or by two substituents which, together with the carbon atom to which they are attached, form a 5- or 6-membered carbocycle, $R^{13D}$ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl, $R^{14D}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl, $R^{15D}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl, $X^{1D}$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy, $X^{2D}$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy, $X^{3D}$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy, t preferably represents the numbers 0, 1, 2, 3 or 4, v preferably represents the numbers 0, 1, 2 or 3, $R^{16D}$ preferably represents hydrogen, methyl, ethyl, n- or i-propyl, $R^{17D}$ preferably represents hydrogen, methyl, ethyl, n- or i-propyl, $R^{18D}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyl-oxy, cyclopropylthio, cyclobutylthio, cyclopentylthio, cyclohexylthio, cyclopropylamino, cyclobutylamino, cyclopentylamino or cyclohexylamino, $R^{19D}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl, $R^{20D}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butyinyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl, n-, i-, s- or t-butyl-, trifluoromethyl-, methoxy-, ethoxy-, n- or i-propoxy-, difluoromethoxy- or trifluoromethoxy-substituted phenyl, or together with $R^{19}$ represents in each case optionally methyl- or ethyl-substituted butane-1,4-diyl (trimethylene), pentane-1,5-diyl, 1-oxabutane-1,4-diyl or 3-oxapentane-1,5-diyl, $X^{4D}$ preferably represents nitro, cyano, carboxyl, carbamoyl, formyl, sulfamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy, $X^{5D}$ preferably represents nitro, cyano, carboxyl, carbamoyl, formyl, sulfamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IV-a) very particularly preferred as herbicide safeners according to the invention are listed in the table below.

Specifically, particular mention may be made of the following compounds of the formula (IV-a):

TABLE 6

(IV-a)

| No. | $X^{1D}_r$ | $A^{1D}$ | $R^{8D}$ |
|---|---|---|---|
| IV-a-1 | 2-Cl, 4-Cl | 1-methyl-3-methyl-5-methyl-5-(methoxycarbonyl)-4,5-dihydropyrazol-5-yl | OCH$_3$ |
| IV-a-2 | 2-Cl, 4-Cl | 1-methyl-3-methyl-5-methyl-5-(ethoxycarbonyl)-4,5-dihydropyrazol-5-yl | OCH$_3$ |
| IV-a-3 | 2-Cl, 4-Cl | 1-methyl-3-methyl-5-methyl-5-(methoxycarbonyl)-4,5-dihydropyrazol-5-yl | OC$_2$H$_5$ |
| IV-a-4 | 2-Cl, 4-Cl | 1-methyl-3-methyl-5-methyl-5-(ethoxycarbonyl)-4,5-dihydropyrazol-5-yl | OC$_2$H$_5$ |
| IV-a-5 | 2-Cl | 1-methyl-3-methyl-5-phenylpyrazol-5-yl | OCH$_3$ |
| IV-a-6 | 2-Cl, 4-Cl | 1-methyl-3-methyl-4-phenylpyrazol-5-yl | OCH$_3$ |
| IV-a-7 | 2-F | 1-methyl-3-methyl-5-phenylpyrazol-5-yl | OCH$_3$ |
| IV-a-8 | 2-F | 1-methyl-3-methyl-5-(2-chlorophenyl)pyrazol-5-yl | OCH$_3$ |
| IV-a-9 | 2-Cl, 4-Cl | 1-methyl-3-methyl-5-(trichloromethyl)-1,2,4-triazol-5-yl | OC$_2$H$_5$ |

TABLE 6-continued (IV-a)

[Structure: X¹ᴰᵣ-phenyl-A¹ᴰ-C(=O)-R⁸ᴰ]

| No. | $X^{1D}_r$ | $A^{1D}$ | $R^{8D}$ |
|---|---|---|---|
| IV-a-10 | 2-Cl, 4-CF₃ | 1-methyl-3-methyl-1,2,4-triazol-5-yl (phenyl-substituted) | OCH₃ |
| IV-a-11 | 2-Cl | 1-methyl-3-methyl-pyrazol-5-yl with 2-F phenyl | OCH₃ |
| IV-a-12 | — | 3-methyl-5-phenyl-4,5-dihydroisoxazol-5-yl (with methyl) | OC₂H₅ |
| IV-a-13 | 2-Cl, 4-Cl | 1-methyl-3-methyl-5-(CH₃)-pyrazole | OC₂H₅ |
| IV-a-14 | 2-Cl, 4-Cl | 1-methyl-3-methyl-5-(i-C₃H₇)-pyrazole | OC₂H₅ |
| IV-a-15 | 2-Cl, 4-Cl | 1-methyl-3-methyl-5-(t-C₄H₉)-pyrazole | OC₂H₅ |
| IV-a-16 | 2-Cl, 4-Cl | 3-methyl-5-(CH₂—)-4,5-dihydroisoxazole | OC₂H₅ |
| IV-a-17 | 2-Cl, 4-Cl | 3-methyl-5-methyl-4,5-dihydroisoxazole | OC₂H₅ |
| IV-a-18 | — | 3-methyl-5-phenyl-4,5-dihydroisoxazol-5-yl (with methyl) | OH |

Specifically, particular mention may furthermore be made of the following compounds of the formula (IV-b):

TABLE 7

(IV-b)

[Structure: quinoline with X³ᴰ and X²ᴰ substituents, 8-O-A²ᴰ-C(=O)-R⁹ᴰ]

| No. | $X^{2D}$ | $X^{3D}$ | $A^{2D}$ | $R^{9D}$ |
|---|---|---|---|---|
| IV-b-1 | 5-Cl | H | CH₂ | OH |
| IV-b-2 | 5-Cl | H | CH₂ | OCH₃ |
| IV-b-3 | 5-Cl | H | CH₂ | OC₂H₅ |
| IV-b-4 | 5-Cl | H | CH₂ | OC₃H₇-n |
| IV-b-5 | 5-Cl | H | CH₂ | OC₃H₇-i |
| IV-b-6 | 5-Cl | H | CH₂ | OC₄H₉-n |
| IV-b-7 | 5-Cl | H | CH₂ | OCH(CH₃)C₅H₁₁-n |
| IV-b-8 | 5-Cl | 2-F | CH₂ | OH |
| IV-b-9 | 5-Cl | 2-Cl | CH₂ | OH |
| IV-b-10 | 5-Cl | H | CH₂ | OCH₂CH=CH₂ |
| IV-b-11 | 5-Cl | H | CH₂ | OC₄H₉-i |
| IV-b-12 | 5-Cl | H | CH₂ | OCH(CH₃)CH₂OCH₂CH=CH₂ |
| IV-b-13 | 5-Cl | H | CH₂ (with allyl isobutyrate group) | OCH₂CH=CH₂ |
| IV-b-14 | 5-Cl | H | C₂H₅ (with isobutyrate group) | OC₂H₅ |
| IV-b-15 | 5-Cl | H | CH₃ (with isobutyrate group) | OCH₃ |

Specifically, particular mention may furthermore be made of the following compounds of the formula (IV-c):

TABLE 8

(IV-c)

[Structure: R¹⁰ᴰ-C(=O)-N(R¹¹ᴰ)(R¹²ᴰ)]

| No. | $R^{10D}$ | $N(R^{11D}R^{12D})$ |
|---|---|---|
| IV-c-1 | CHCl₂ | N(CH₂CH=CH₂)₂ |
| IV-c-2 | CHCl₂ | 2,2-dimethyl-3-methyl-oxazolidine |

TABLE 8-continued (IV-c)

$$R^{10D}-C(=O)-N(R^{11D})(R^{12D})$$

| No. | $R^{10D}$ | $N(R^{11D}R^{12D})$ |
|---|---|---|
| IV-c-3 | CHCl$_2$ | 2,2,5-trimethyl-oxazolidin-3-yl (H$_3$C, CH$_3$, CH$_3$) |
| IV-c-4 | CHCl$_2$ | 4-methyl-1-oxa-4-azaspiro[4.5]decan-4-yl |
| IV-c-5 | CHCl$_2$ | 2,2-dimethyl-3-methyl-5-phenyl-oxazolidin-3-yl (H$_3$C, CH$_3$, C$_6$H$_5$) |
| IV-c-6 | CHCl$_2$ | 3,4-dimethyl-3,4-dihydro-2H-benzo[1,4]oxazin-4-yl |
| IV-c-7 | CHCl$_2$ | 2,2-dimethyl-3-methyl-5-(furan-2-yl)-oxazolidin-3-yl |

Specifically, particular mention may furthermore be made of the following compounds of the formula (IV-d):

TABLE 9

(IV-d)

Structure: R$^{18D}$–C(=O)–N(R$^{17D}$)–[phenyl-X$^{5D}_v$]–SO$_2$–N(R$^{16D}$)–C(=O)–[phenyl-X$^{4D}_t$]

| No. | $R^{16D}$ | $R^{17D}$ | $R^{18D}$ | $X^{4D}_t$ | $X^{5D}_v$ |
|---|---|---|---|---|---|
| IV-d-1 | H | H | CH$_3$ | 2-OCH$_3$ | — |
| IV-d-2 | H | H | C$_2$H$_5$ | 2-OCH$_3$ | — |
| IV-d-3 | H | H | C$_3$H$_7$-n | 2-OCH$_3$ | — |
| IV-d-4 | H | H | C$_3$H$_7$-i | 2-OCH$_3$ | — |
| IV-d-5 | H | H | cyclopropyl | 2-OCH$_3$ | — |
| IV-d-6 | H | H | CH$_3$ | 2-OCH$_3$, 5-CH$_3$ | — |
| IV-d-7 | H | H | C$_2$H$_5$ | 2-OCH$_3$, 5-CH$_3$ | — |
| IV-d-8 | H | H | C$_3$H$_7$-n | 2-OCH$_3$, 5-CH$_3$ | — |
| IV-d-9 | H | H | C$_3$H$_7$-i | 2-OCH$_3$, 5-CH$_3$ | — |
| IV-d-10 | H | H | cyclopropyl | 2-OCH$_3$, 5-CH$_3$ | — |
| IV-d-11 | H | H | OCH$_3$ | 2-OCH$_3$, 5-CH$_3$ | — |
| IV-d-12 | H | H | OC$_2$H$_5$ | 2-OCH$_3$, 5-CH$_3$ | — |
| IV-d-13 | H | H | OC$_3$H$_7$-i | 2-OCH$_3$, 5-CH$_3$ | — |
| IV-d-14 | H | H | SCH$_3$ | 2-OCH$_3$, 5-CH$_3$ | — |
| IV-d-15 | H | H | SC$_2$H$_5$ | 2-OCH$_3$, 5-CH$_3$ | — |
| IV-d-16 | H | H | SC$_3$H$_7$-i | 2-OCH$_3$, 5-CH$_3$ | — |
| IV-d-17 | H | H | NHCH$_3$ | 2-OCH$_3$, 5-CH$_3$ | — |
| IV-d-18 | H | H | NHC$_2$H$_5$ | 2-OCH$_3$, 5-CH$_3$ | — |
| IV-d-19 | H | H | NHC$_3$H$_7$-i | 2-OCH$_3$, 5-CH$_3$ | — |
| IV-d-20 | H | H | N(H)(CH$_3$)(cyclopropyl) | 2-OCH$_3$, 5-CH$_3$ | — |
| IV-d-21 | H | H | NHCH$_3$ | 2-OCH$_3$ | — |
| IV-d-22 | H | H | NHC$_3$H$_7$-i | 2-OCH$_3$ | — |
| IV-d-23 | H | H | N(CH$_3$)$_2$ | 2-OCH$_3$ | — |
| IV-d-24 | H | H | N(CH$_3$)$_2$ | 3-CH$_3$, 4-CH$_3$ | — |
| IV-d-25 | H | H | CH$_2$—O—CH$_3$ | 2-OCH$_3$ | — |

Specifically, particular mention may furthermore be made of the following compounds of the formula (IV-e):

TABLE 10

(IV-e)

Structure: R$^{19D}$R$^{20D}$N–C(=O)–[phenyl-X$^{5D}_v$]–SO$_2$–N(R$^{18D}$)–C(=O)–[phenyl-X$^{4D}_t$]

| No. | $R^{16D}$ | $R^{19D}$ | $R^{20D}$ | $X^{4D}_t$ | $X^{5D}_v$ |
|---|---|---|---|---|---|
| IV-e-1 | H | H | CH$_3$ | 2-OCH$_3$ | — |
| IV-e-2 | H | H | C$_2$H$_5$ | 2-OCH$_3$ | — |
| IV-e-3 | H | H | C$_3$H$_7$-n | 2-OCH$_3$ | — |
| IV-e-4 | H | H | C$_3$H$_7$-i | 2-OCH$_3$ | — |
| IV-e-5 | H | H | cyclopropyl | 2-OCH$_3$ | — |
| IV-e-6 | H | CH$_3$ | CH$_3$ | 2-OCH$_3$ | — |
| IV-e-7 | H | CH$_3$ | CH$_3$ | 2-OCH$_3$, 5-CH$_3$ | — |
| IV-e-8 | H | H | C$_2$H$_5$ | 2-OCH$_3$, 5-CH$_3$ | — |

TABLE 10-continued

(IV-e)

| No. | $R^{16D}$ | $R^{19D}$ | $R^{20D}$ | $X^{4D}_t$ | $X^{5D}_v$ |
|---|---|---|---|---|---|
| IV-e-9 | H | H | $C_3H_7$-n | 2-OCH$_3$, 5-CH$_3$ | — |
| IV-e-10 | H | H | $C_3H_7$-i | 2-OCH$_3$, 5-CH$_3$ | — |
| IV-e-11 | H | H | ◁ | 2-OCH$_3$, 5-CH$_3$ | — |
| IV-e-12 | H | CH$_3$ | CH$_3$ | 2-OCH$_3$, 5-CH$_3$ | — |

The crop plant compatibility-improving compounds [component b)] which are most preferred are cloquintocet-mexyl, fenchlorazole-ethyl, isoxadifen-ethyl, mefenpyr-diethyl, furilazole, fenclorim, cumyluron, dymron, dimepiperate and the compounds IV-e-5 and IV-e-11, cloquintocet-mexyl and mefenpyr-diethyl being especially preferred. Special preference is furthermore given to isoxadifen-ethyl and IV-e-5.

Examples of selective insecticidal and/or acaricidal combinations according to the invention of in each case one active compound of the formula (I) and in each case one of the safeners defined above are listed in the table below.

TABLE 11

Examples of combinations according to the invention

| Active compound of the formula (I), (II) or (III) | Safener |
|---|---|
| (I-a-1) | cloquintocet-mexyl |
| (I-a-1) | fenchlorazole-ethyl |
| (I-a-1) | isoxadifen-ethyl |
| (I-a-1) | mefenpyr-diethyl |
| (I-a-1) | furilazole |
| (I-a-1) | fenclorim |
| (I-a-1) | cumyluron |
| (I-a-1) | daimuron/dymron |
| (I-a-1) | dimepiperate |
| (I-a-1) | IV-e-11 |
| (I-a-1) | IV-e-5 |
| (I-a-2) | cloquintocet-mexyl |
| (I-a-2) | fenchlorazole-ethyl |
| (I-a-2) | isoxadifen-ethyl |
| (I-a-2) | mefenpyr-diethyl |
| (I-a-2) | furilazole |
| (I-a-2) | fenclorim |
| (I-a-2) | cumyluron |
| (I-a-2) | daimuron/dymron |
| (I-a-2) | dimepiperate |
| (I-a-2) | IV-e-11 |
| (I-a-2) | IV-e-5 |
| (I-a-45) | cloquintocet-mexyl |
| (I-a-45) | fenchlorazole-ethyl |
| (I-a-45) | isoxadifen-ethyl |
| (I-a-45) | mefenpyr-diethyl |
| (I-a-45) | furilazole |
| (I-a-45) | fenclorim |
| (I-a-45) | cumyluron |
| (I-a-45) | daimuron/dymron |
| (I-a-45) | dimepiperate |
| (I-a-45) | IV-e-11 |
| (I-a-45) | IV-e-5 |
| (I-a-55) | cloquintocet-mexyl |
| (I-a-55) | fenchlorazole-ethyl |
| (I-a-55) | isoxadifen-ethyl |
| (I-a-55) | mefenpyr-diethyl |
| (I-a-55) | furilazole |
| (I-a-55) | fenclorim |
| (I-a-55) | cumyluron |
| (I-a-55) | daimuron/dymron |
| (I-a-55) | dimepiperate |
| (I-a-55) | IV-e-11 |
| (I-a-55) | IV-e-5 |
| (I-b-2) | cloquintocet-mexyl |
| (I-b-2) | fenchlorazole-ethyl |
| (I-b-2) | isoxadifen-ethyl |
| (I-b-2) | mefenpyr-diethyl |
| (I-b-2) | furilazole |
| (I-b-2) | fenclorim |
| (I-b-2) | cumyluron |
| (I-b-2) | daimuron/dymron |
| (I-b-2) | dimepiperate |
| (I-b-2) | IV-e-11 |
| (I-b-2) | IV-e-5 |
| (II-3) | cloquintocet-mexyl |
| (II-3) | fenchlorazole-ethyl |
| (II-3) | isoxadifen-ethyl |
| (II-3) | mefenpyr-diethyl |
| (II-3) | furilazole |
| (II-3) | fenclorim |
| (II-3) | cumyluron |
| (II-3) | daimuron/dymron |
| (II-3) | dimepiperate |
| (II-3) | IV-e-11 |
| (II-3) | IV-e-5 |
| (II-6) | cloquintocet-mexyl |
| (II-6) | fenchlorazole-ethyl |
| (II-6) | isoxadifen-ethyl |
| (II-6) | mefenpyr-diethyl |
| (II-6) | furilazole |
| (II-6) | fenclorim |
| (II-6) | cumyluron |
| (II-6) | daimuron/dymron |
| (II-6) | dimepiperate |
| (II-6) | IV-e-11 |
| (II-6) | IV-e-5 |
| (III-a-4) | cloquintocet-mexyl |
| (III-a-4) | fenchlorazole-ethyl |
| (III-a-4) | isoxadifen-ethyl |
| (III-a-4) | mefenpyr-diethyl |
| (III-a-4) | furilazole |
| (III-a-4) | fenclorim |
| (III-a-4) | cumyluron |
| (III-a-4) | daimuron/dymron |
| (III-a-4) | dimepiperate |
| (III-a-4) | IV-e-11 |
| (III-a-4) | IV-e-5 |
| (III-a-9) | cloquintocet-mexyl |
| (III-a-9) | fenchlorazole-ethyl |
| (III-a-9) | isoxadifen-ethyl |
| (III-a-9) | mefenpyr-diethyl |
| (III-a-9) | furilazole |
| (III-a-9) | fenclorim |
| (III-a-9) | cumyluron |
| (III-a-9) | daimuron/dymron |
| (III-a-9) | dimepiperate |
| (III-a-9) | IV-e-11 |
| (III-a-9) | IV-e-5 |

The compounds of the general formula (IV-a) to be used as safeners are known and/or can be prepared by processes known per se (cf. WO 91/07874, WO 95/07897).

The compounds of the general formula (IV-b) to be used as safeners are known and/or can be prepared by processes known per se (cf. EP-A 0 191 736).

The compounds of the general formula (IV-c) to be used as safeners are known and/or can be prepared by processes known per se (cf. DE-A 2218 097, DE-A 23 50 547).

The compounds of the general formula (IV-d) to be used as safeners are known and/or can be prepared by processes known per se (cf. DE-A 196 21522, U.S. Pat. No. 6,235,680).

The compounds of the general formula (IV-e) to be used as safeners are known and/or can be prepared by processes known per se (cf. WO 99/66795, U.S. Pat. No. 6,251,827).

Surprisingly, it has now been found that the active compound combinations, defined above, of haloalkylnicotinic acid derivatives of the general formula (I), phthalic acid diamides of the formula (II) or anthranilamides of the formula (III) and safeners (antidotes) of group (b) listed above have very good insecticidal and/or acaricidal activity, are very well tolerated by useful plants and can be used in various crops for the selective control of insects.

Here, it has to be considered to be entirely surprising that the compounds of group (b) listed above are in some cases capable of increasing the insecticidal and/or acaricidal activity of the haloalkylnicotinic acid derivatives of the general formula (I), the phthalic acid diamides of the general formula (II) or the anthranilamides of the general formula (III) such that a synergistic effect is observed.

The combinations of active compounds can generally be used, for example, for the following plants:

Dicotyledonous crops of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cuburbita, Helianthus.*

Monocotyledonous crops of the genera: *Oryza, Zea, Triticum, Hordeum, Avena, Secale, Sorghum, Panicum, Saccharum, Ananas, Asparagus, Allium.*

However, the use of the combination of active compounds is by no means limited to these genera but equally also extends to other plants.

The advantageous effect of the crop plant compatibility of the combinations of active compounds is particularly strongly pronounced at certain concentration ratios. However, the weight ratios of the active compounds in the combinations of active compounds can be varied within relatively wide ranges. In general, 0.001 to 1000 parts by weight, preferably 0.01 to 100 parts by weight, particularly preferably 0.05 to 10 parts by weight and most preferably 0.07 to 1.5 parts by weight of one of the crop plant compatibility-improving compounds (antidotes/safeners) mentioned above under (b) are present per part by weight of active compound of the formula (I) or (II) or (III).

The active compounds or combinations of active compounds can be converted into the customary formulations, such as solutions, emulsions, wettable powders, suspensions, powders, dusts, pastes, soluble powders, granules, suspoemulsion concentrates, natural and synthetic materials impregnated with active compounds and microencapsulations in polymeric materials.

These formulations are produced in a known manner, for example by mixing the active compounds with extenders, that is, liquid solvents and/or solid carriers, optionally with the use of surface-active agents, that is, emulsifiers and/or dispersants and/or foam formers.

If the extender used is water, it is also possible to use for example organic solvents as auxiliary solvents. Suitable liquid solvents are mainly: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and ethers and esters thereof; ketones, such as acetone, methyl ethyl ketone, methyl isobutyl ketone or cyclohexanone, strongly polar solvents, such as dimethylformamide and dimethyl sulfoxide, and water.

Suitable solid carriers are:

for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable as solid carriers for granules are: for example crushed and fractionated natural rocks such as calcite, marble, pumice, sepiolite and dolomite, and synthetic granules of inorganic and organic meals, and granules of organic material such as sawdust, coconut shells, corn cobs and tobacco stalks; suitable as emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolysates; suitable as dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95% by weight of active compound, preferably between 0.5 and 90%.

The combinations of active compounds are generally applied in the form of ready-to-use formulations. However, the active compounds contained in the combinations of active compounds may also be applied in the form of individual formulations which are mixed upon use, that is, in the form of tank mixes.

The combinations of active compounds, as such or in their formulations, may furthermore also be used as a mixture with other known herbicides, again with ready-to-use formulations or tank mixes being possible. A mixture with other known active compounds, such as fungicides, insecticides, acaricides, nematicides, attractants, sterilants, bactericides, bird repellents, growth substances, plant nutrients and soil conditioners is also possible. It may furthermore be advantageous for specific applications, in particular for the post-emergence method, to incorporate into the formulations plant-compatible mineral or vegetable oils (for example the commercial product "Rako Binol") or ammonium salts, such as, for example, ammonium sulfate or ammonium thiocyanate, as further additives.

The combinations of active compounds can be used as such, in the form of their formulations or the use forms which can be prepared from these formulations by further dilution, such as ready-to-use solutions, suspensions, emulsions, powders, pastes and granules. Application is effected in the customary manner, for example by watering, spraying, atomizing, dusting or broadcasting.

The application rates of the combination of active compounds can be varied within a certain range; they depend, inter alia, on the weather and the soil factors. In general, the application rates are from 0.005 to 5 kg per ha, preferably from 0.01 to 2 kg per ha, particularly preferably from 0.05 to 1.0 kg per ha.

The combinations of active compounds can be applied before and after emergence of the plants, i.e. by the pr-emergence and the post-emergence method.

Depending on their properties, the safeners to be used can be employed for pretreating the seed of the crop plant (seed dressing) or be incorporated into the seed furrows before sowing or, together with the herbicide, be applied before or after emergence of the plants.

The combinations of active compounds are suitable for controlling animal pests, preferably arthropods and nematodes, in particular insects and arachnids, encountered in agriculture, animal health in forests, in stored-product and material protection and in the hygiene sector. They are effective against normally sensitive and resistant species and against all or individual stages of development. The above-mentioned pests include:

From the order of the Isopoda, for example, *Oniscus asellus, Armadillidium vulgare, Porcellio scaeale*.

From the order of the Diplopoda, for example, *Blaniulus guttulatus*.

From the order of the Chilopoda, for example, *Geophilus carpophagus, Scutigera* spp.

From the order of the Symphyla, for example, *Scutigerella immaculata*.

From the order of the Thysamnra, for example, *Lepisma saccharina*.

From the order of the Collembola, for example, *Onychiurus armatus*.

From the order of the Orthoptera, for example, *Acheta domesticus, Gryllotalpa* app., *Locusta migratoria migratorioides, Melanoplus* spp., *Schistocerca gregaria*.

From the order of the Blattaria, for example, *Blatta orientalis, Periplaneta americana, Leucophaea maderae, Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis*.

From the order of the Heteroptera, for example, *Eurygaster* spp., *Dysderous intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus anmdinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Chematobia bnunmata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citreila, Agrotis* spp., *Euxoa* spp., *Feltia* spp., *Earias insulana, Heliothis* spp., *Mamestra brassicae, Panolis flammes, Spodoptera* spp., *Trichoplusia ni, Carpocapsa pomonella, Pieris* spp., *Chilo* spp., *Pyrausta nubilalis, Ephestia lkehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae*.

From the order of the Coleoptera, for example, *Anobium puncttum, Rhizopertha dominica, Bruchidius obtectus, Acanthosceides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzacphilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meigethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus*.

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* app., *Culex* app., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

From the class of the arachnids, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsoncmus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

When used as insecticides, the combinations of active compounds can furthermore be present, in their commercial formulations and in the use forms prepared from these formulations, as a mixture with synergists. Synergists are compounds which enhance the activity of the active compounds, without it being necessary for the added synergist to be active for its part.

The content of active compounds of the use forms prepared from the commercial formulations may vary within wide ranges. The concentration of active compounds of the use forms may be from 0.0000001 to 95% by weight of active compound and is preferably from 0.0001 to 1% by weight.

Application is carried out in a customary manner adapted to the use forms.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeder's certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

As already mentioned above, it is possible to treat all plants and their parts according to the invention. In a preferred embodiment, wild plant species and plant varieties, or those obtained by conventional biological breeding methods, such as crossing or protoplast fusion, and parts thereof, are treated. In a further preferred embodiment, transgenic plants and plant varieties obtained by genetic engineering, if appropriate in combination with conventional methods (Genetic Modified Organisms), and parts thereof are treated. The term "parts" or "parts of plants" or "plant parts" has been explained above.

Particularly preferably, plants of the plant varieties which are in each case commercially available or in use are treated according to the invention.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant varieties (i.e. those obtained by genetic engineering) which are preferred and to be treated according to the invention include all plants which, in the genetic modification, received genetic material which imparts particularly advantageous useful traits to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), corn, soybeans, potatoes, cotton, oilseed rape and also fruit plants (with the fruits apples, pears, citrus fruits and grapes), and particular emphasis is given to corn, soybeans, potatoes, cotton and oilseed rape. Traits that are particularly emphasized are the increased defense of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidamolinones, sulfonylureas, glyphosate or phosphinotricin (for example the "PAT" gene). The genes which impart the desired traits in question can also be present in combination with one another in the transgenic plants. Examples of "Bt plants" which may be mentioned are corn varieties, cotton varieties, soybean varieties and potato varieties which are sold under the trade names YIELD GARD® (for example corn, cotton, soyabeans), KnockOut® (for example corn), StarLink® (for example corn), Bollgard® (cotton), Nucotn® (cotton) and NewLeaf® (potato). Examples of herbicide-tolerant plants which may be mentioned are corn varieties, cotton varieties and soybean varieties which are sold under the trade names Roundup Ready® (tolerance to glyphosate, for example corn, cotton, soybean), Liberty Link® (tolerance to phosphinotricin, for example oilseed rape), IMI® (tolerance to imidazolinones) and STS® (tolerance to sulfonylureas, for example corn). Herbicide-resistant plants (plants bred in a conventional manner for herbicide tolerance) which may be mentioned include the varieties sold under the name Clearfield® (for example corn). Of course, these statements also apply to plant varieties having these or still-to-be-developed genetic traits, which plants will be developed and/or marketed in the future.

The plants listed can be treated according to the invention in a particularly advantageous manner with the active compound mixtures. The preferred ranges stated above for the mixtures also apply to the treatment of these plants. Particular emphasis is given to the treatment of plants with the mixtures specifically mentioned in the present text.

Formula for Calculating the Kill Rate of a Combination of Two Active Compounds

The expected activity for a given combination of two active compounds can be calculated (cf. Colby, S. R.; "Calculating Synergistic and Antagonistic Responses of Herbicide Combinations", Weeds 15, pages 20-22, 1967):

if $X$=the kill rate, expressed in % of the untreated control, when employing active compound A at an application rate of m ppm, $Y$=the kill rate, expressed in % of the untreated control, when employing active compound B at an application rate of n ppm, E=the kill rate, expressed in % of the untreated control, when employing active compounds A and B at application rates of m and n ppm,
then $$E = X + Y - \frac{X \times Y}{100}$$

If the actual insecticidal kill rate is higher than the calculated one, the kill of the combination is superadditive, i.e. a synergistic effect is present. In this case, the kill rate that is actually observed has to be higher than the value, calculated using the formula above, for the expected kill rate (E).

Examples for Spray Treatment—Dripping Wet
  Solvent: water
  Adjuvant: rapeseed oil methyl ester To produce a suitable solution, 1 part by weight of formulation is mixed with the stated amount of water and adjuvant and the concentrate is diluted with water to the desired concentration.

*Heliothis armigera* Test

Cotton plants (*Gossypium hirsutum*) are sprayed to runoff point with the desired use concentration and populated with caterpillars of the cotton bollworm (*Heliothis armigera*) while the leaves are still moist.

*Spodoptera frugiperda* Test

Corn plants (*Zea mais*) are sprayed to runoff point with the desired use concentration and populated with caterpillars of the armyworm (*Spodoptera frugiperda*) while the leaves are still moist.

*Plutella xylostella* Test

Cabbage plants (*Brassica pekinesis*) are sprayed to runoff point with the desired use concentration and populated with larvae of the diamondback moth (*Plutella xylostella*) while the leaves are still moist.

After the desired period of time, the kill in % is determined. 100% means that all larvae have been killed; 0% means that none of the larvae have been killed. The determined kill rates are entered into Colby's formula (see above).

In this test, for example, the following combinations according to the present application show a synergistically enhanced activity compared to the components applied on their own:

TABLE A1

Plant-damaging insects
*Heliothis armigera* test

| Formulation | Concentration in ppm | Kill in % after $7^d$ | |
|---|---|---|---|
| II-6 | 0.032 | 50 | |
| isoxadifen-ethyl WG 50 | 25 | 0 | |
| II-6 + isoxadifen-ethyl (1:781.25) | | found* | calc.** |
| according to the invention | 0.032 + 25 | 100 | 50 |
| IV-e-5 a.i. | 100 | 0 | |
| II-6 + IV-e-5 (1:3125) | | found* | calc.** |
| according to the invention | 0.032 + 100 | 100 | 50 |
| dichlormid a.i. | 100 | 0 | |
| II-6 + dichlormid (1:3125) | | found* | calc.** |
| according to the invention | 0.032 + 100 | 100 | 50 |
| furilazole a.i. | 25 | 0 | |
| II-6 + furilazole (1:781.25) | | found* | calc.** |
| according to the invention | 0.032 + 25 | 100 | 50 |

*found = activity found
**calc. = activity calculated using Colby's formula

TABLE A2

Plant-damaging insects
*Heliothis armigera* test

| Formulation | Concentration in ppm | Kill in % after $3^d$ | |
|---|---|---|---|
| II-3 | 0.16 | 60 | |
| isoxadifen-ethyl WG 50 | 100 | 0 | |
| II-3 + isoxadifen-ethyl (1:625) | | found* | calc.** |
| according to the invention | 0.16 + 100 | 83 | 60 |
| mefenpyr WG 15 | 100 | 0 | |
| II-3 + mefenpyr (1:625) | | found* | calc.** |
| according to the invention | 0.16 + 100 | 100 | 60 |
| IV-e-5 a.i. | 50 | 0 | |
| II-3 + IV-e-5 (1:312.5) | | found* | calc.** |
| according to the invention | 0.16 + 50 | 83 | 60 |
| cloquintocet-mexyl WP 20 | 50 | 0 | |
| II-3 + cloquintocet-mexyl (1:312.5) | | found* | calc.** |
| according to the invention | 0.16 + 50 | 100 | 60 |
| dichlormid a.i. | 100 | 0 | |
| II-3 + dichlormid (1:625) | | found* | calc.** |
| according to the invention | 0.16 + 100 | 83 | 60 |
| fenclorim a.i. | 100 | 0 | |
| II-3 + fenclorim (1:625) | | found* | calc.** |
| according to the invention | 0.16 + 100 | 100 | 60 |
| furilazole a.i. | 50 | 0 | |
| II-3 + furilazole (1:312.5) | | found* | calc.** |
| according to the invention | 0.16 + 50 | 100 | 60 |

*found = activity found
**calc. = activity calculated using Colby's formula

TABLE B1

Plant-damaging insects
*Plutella xylostella* test

| Formulation | Concentration in ppm | Kill in % after $7^d$ | |
|---|---|---|---|
| II-6 | 0.032 | 33 | |
| IV-e-5 a.i. | 100 | 0 | |
| II-6 + IV-e-5 (1:3125) | | found* | calc.** |
| according to the invention | 0.032 + 100 | 100 | 33 |
| fenclorim a.i. | 25 | 0 | |
| II-6 + fenclorim (1:781.25) | | found* | calc.** |
| according to the invention | 0.032 + 25 | 60 | 33 |
| furilazole a.i. | 50 | 0 | |
| II-6 + furilazole (1:1562.5) | | found* | calc.** |
| according to the invention | 0.032 + 50 | 100 | 33 |

*found = activity found
**calc. = activity calculated using Colby's formula

TABLE B2

Plant-damaging insects
*Plutella xylostella* test

| Formulation | Concentration in ppm | Kill in % after 3$^d$ | |
|---|---|---|---|
| II-3 | 0.032 | 30 | |
| Isoxadifen-ethyl WG 50 | 100 | 0 | |
| II-3 + isoxadifen-ethyl (1:3125) | | found* | calc.** |
| according to the invention | 0.032 + 100 | 83 | 30 |
| mefenpyr WG 15 | 50 | 0 | |
| II-3 + mefenpyr (1:1562.5) | | found* | calc.** |
| according to the invention | 0.032 + 50 | 60 | 30 |
| cloquintocet-mexyl WP 20 | 50 | 0 | |
| II-3 + cloquintocet-mexyl (1:1562.5) | | found* | calc.** |
| according to the invention | 0.032 + 50 | 90 | 30 |
| dichlormid a.i. | 100 | 0 | |
| II-3 + dichlormid (1:3125) | | found* | calc.** |
| according to the invention | 0.032 + 100 | 50 | 30 |

*found = activity found
**calc. = activity calculated using Colby's formula

TABLE C1

Plant-damaging insects
*Spodoptera frugiperda* test

| Formulation | Concentration in ppm | Kill in % after 7$^d$ | |
|---|---|---|---|
| II-6 | 0.032 | 0 | |
| isoxadifen-ethyl WG 50 | 50 | 0 | |
| II-6 + isoxadifen-ethyl (1:1562.5) | | found* | calc.** |
| according to the invention | 0.032 + 50 | 66 | 0 |
| mefenpyr WG 15 | 25 | 0 | |
| II-6 + mefenpyr (1:781.25) | | found* | calc.** |
| according to the invention | 0.032 + 25 | 100 | 0 |
| IV-e-5 a.i. | 100 | 0 | |
| II-6 + IV-e-5 (1:3125) | | found* | calc.** |
| according to the invention | 0.032 + 100 | 100 | 0 |

*found = activity found
**calc. = activity calculated using Colby's formula

TABLE C2

Plant-damaging insects *Spodoptera frugiperda* test

| Formulation | Concentration in ppm | Kill in % after 3$^d$ | |
|---|---|---|---|
| II-3 | 0.16 | 50 | |
| isoxadifen-ethyl WG 50 | 100 | 0 | |
| II-3 + isoxadifen-ethyl (1:625) | | found* | calc.** |
| according to the invention | 0.16 + 100 | 100 | 50 |
| mefenpyr WG 15 | 100 | 0 | |
| II-3 + mefenpyr (1:625) | | found* | calc.** |
| according to the invention | 0.16 + 100 | 100 | 50 |
| IV-e-5 a.i. | 100 | 0 | |
| II-3 + IV-e-5 (1:625) | | found* | calc.** |
| according to the invention | 0.16 + 100 | 100 | 50 |
| cloquintocet-mexyl WP 20 | 50 | 0 | |
| II-3 + cloquintocet-mexyl (1:312.5) | | found* | calc.** |
| according to the invention | 0.16 + 50 | 83 | 50 |
| dichlormid a.i. | 100 | 0 | |
| II-3 + dichlormid (1:625) | | found* | calc.** |
| according to the invention | 0.16 + 100 | 100 | 50 |
| fenclorim a.i. | 100 | 0 | |
| II-3 + fenclorim (1:625) | | found* | calc.** |
| according to the invention | 0.16 + 100 | 83 | 50 |
| furilazole a.i. | 100 | 0 | |
| II-3 + furilazole (1:625) | | found* | calc.** |
| according to the invention | 0.16 + 100 | 180 | 50 |

*found = activity found
**calc. = activity calculated using Colby's formula

Examples of the Spray Application—Dripping Wet

Solvent: water

Adjuvant: rapeseed oil methyl ester

To produce a suitable application solution, 1 part by weight of the formulation is mixed with the appropriate amount of water and the adjuvant and the concentrate is diluted with water to the desired concentration.

*Aphis gossypii* Test

Cotton plants (*Gossypium herbaceum*) which are heavily infested by the cotton aphid (*Aphis gossypii*) are sprayed to runoff point with the desired concentration of the application solution.

*Metopolophium dirhodum* Test

Barley plants (*Hordeum vulgare*) which are heavily infested by a cereal aphid (*Metopolophium dirhodum*) are sprayed to runoff point with the desired concentration of the application solution.

*Myzus persicae* Test

Bell pepper plants (*Capsicum sativum*) which are heavily infested by the green peach aphid (*Myzus persicae*) are sprayed to runoff point with the desired concentration of the application solution.

After the desired period of time, the kill in % is determined. 100% means that all aphids have been killed; 0% means that none of the aphids have been killed. The determined kill rates are entered into Colby's formula (see sheet 1).

In this test, for example, the following combinations of active compounds according to the present application show a synergistically enhanced activity compared to the components applied on their own:

TABLE D1

Plant-damaging insects
*Aphis gossypii* test

| Formulation | Concentration in ppm | Kill in % after 7$^d$ | |
|---|---|---|---|
| I-a-45 | 20 | 60 | |
| dichlormid a.i. | 100 | 0 | |
| I-a-45 + dichlormid (1:5) | | found* | calc.** |
| according to the invention | 20 + 100 | 90 | 60 |
| fenclorim a.i. | 100 | 0 | |
| I-a-45 + fenclorim (1:5) | | found* | calc.** |
| according to the invention | 20 + 100 | 95 | 60 |
| furilazole a.i. | 100 | 0 | |
| I-a-45 + furilazole (1:5) | | found* | calc.** |
| according to the invention | 20 + 100 | 95 | 60 |

*found = activity found
**calc. = activity calculated using Colby's formula

TABLE D2

Plant-damaging insects
*Aphis gossypii* test

| Formulation | Concentration in ppm | Kill in % after $7^d$ | |
|---|---|---|---|
| I-a-55 | 20 | 65 | |
| | 4 | 15 | |
| mefenpyr WG 15 | 100 | 0 | |
| I-a-55 + mefenpyr (1:5) | | found* | calc.** |
| according to the invention | 20 + 100 | 90 | 65 |
| IV-e-5 a.i. | 100 | 0 | |
| I-a-55 + IV-e-5 (1:25) | | found* | calc.** |
| according to the invention | 4 + 100 | 65 | 15 |
| cloquintocet-mexyl WP 20 | 100 | 5 | |
| I-a-55 + cloquintocet-mexyl (1:25) | | found* | calc.** |
| according to the invention | 4 + 100 | 60 | 15 |
| dichlormid a.i. | 50 | 0 | |
| I-a-55 + dichlormid (1:12.5) | | found* | calc.** |
| according to the invention | 4 + 50 | 65 | 15 |
| fenclorim a.i. | 100 | 0 | |
| I-a-55 + fenclorim (1:25) | | found* | calc.** |
| according to the invention | 4 + 100 | 65 | 15 |
| furilazole a.i. | 100 | 0 | |
| I-a-55 + furilazole (1:25) | | found* | calc.** |
| according to the invention | 4 + 100 | 60 | 15 |

*found = activity found
**calc. = activity calculated using Colby's formula

TABLE E1

Plant-damaging insects
*Metopolophium dirhodum* test

| Formulation | Concentration in ppm | Kill in % after $7^d$ | |
|---|---|---|---|
| I-a-45 | 20 | 20 | |
| dichlormid a.i. | 100 | 0 | |
| I-a-45 + dichlormid (1:5) | | found* | calc.** |
| according to the invention | 20 + 100 | 90 | 20 |
| fenclorim a.i. | 100 | 0 | |
| I-a-45 + fenclorim (1:5) | | found* | calc.** |
| according to the invention | 20 + 100 | 90 | 20 |
| furilazole a.i. | 100 | 0 | |
| I-a-45 + furilazole (1:5) | | found* | calc.** |
| according to the invention | 20 + 100 | 55 | 20 |

*found = activity found
**calc. = activity calculated using Colby's formula

TABLE E2

Plant-damaging insects
*Metopolophium dirhodum* test

| Formulation | Concentration in ppm | Kill in % after $7^d$ | |
|---|---|---|---|
| I-a-55 | 20 | 25 | |
| | 4 | 0 | |
| isoxadifen-ethyl WG 50 | 25 | 0 | |
| I-a-55 + isoxadifen-ethyl (1:6.25) | | found* | calc.** |
| according to the invention | 4 + 25 | 70 | 0 |
| mefenpyr WG 15 | 100 | 0 | |
| I-a-55 + mefenpyr (1:25) | | found* | calc.** |
| according to the invention | 4 + 100 | 75 | 0 |
| IV-e-5 a.i. | 25 | 0 | |
| I-a-55 + IV-e-5 (1:1.25) | | found* | calc.** |
| according to the invention | 20 + 25 | 85 | 25 |
| cloquintocet-mexyl WP 20 | 100 | 0 | |
| I-a-55 + cloquintocet-mexyl (.1:5) | | found* | calc.** |
| according to the invention | 20 + 100 | 90 | 25 |
| dichlormid a.i. | 100 | 0 | |
| I-a-55 + dichlormid (1:5) | | found* | calc.** |
| according to the invention | 20 + 100 | 55 | 25 |
| fenclorim a.i. | 100 | 0 | |
| I-a-55 + fenclorim (1:5) | | found* | calc.** |
| according to the invention | 20 + 100 | 75 | 25 |
| furilazole a.i. | 100 | 0 | |
| I-a-55 + furilazole (1:1.25) | | found* | calc.** |
| according to the invention | 20 + 25 | 55 | 25 |

*found = activity found
**calc. = activity calculated using Colby's formula

TABLE F1

Plant-damaging insects
*Myzus persicae* test

| Formulation | Concentration in ppm | Kill in % after $3^d$ | |
|---|---|---|---|
| I-a-45 | 20 | 30 | |
| | 4 | 5 | |
| dichlormid a.i. | 25 | 0 | |
| I-a-45 + dichlormid (1:6.25) | | found* | calc.** |
| according to the invention | 4 + 25 | 30 | 5 |
| fenclorim a.i. | 25 | 0 | |
| I-a-45 + fenclorim (1:1.25) | | found* | calc.** |
| according to the invention | 20 + 25 | 50 | 30 |
| furilazole a.i. | 100 | 0 | |
| I-a-45 + furilazole (1:5) | | found* | calc.** |
| according to the invention | 20 + 100 | 60 | 30 |

*found = activity found
**calc. = activity calculated using Colby's formula

TABLE F2

Plant-damaging insects
*Myzus persicae* test

| Formulation | Concentration in ppm | Kill in % after $7^d$ | |
|---|---|---|---|
| I-a-55 | 20 | 0 | |
| mefenpyr WG 15 | 100 | 0 | |
| I-a-55 + mefenpyr (1:5) | | found* | calc.** |
| according to the invention | 20 + 100 | 40 | 0 |
| IV-e-5 a.i. | 100 | 0 | |
| I-a-55 + IV-e-5 (1:5) | | found* | calc.** |
| according to the invention | 20 + 100 | 40 | 0 |
| cloquintocet-mexyl WP 20 | 50 | 0 | |
| I-a-55 + cloquintocet-mexyl (1:2.5) | | found* | calc.** |
| according to the invention | 20 + 50 | 40 | 0 |
| dichlormid a.i. | 100 | 0 | |
| I-a-55 + dichlormid (1:5) | | found* | calc.** |
| according to the invention | 20 + 100 | 25 | 0 |
| fenclorim a.i. | 100 | 0 | |
| I-a-55 + fenclorim (1:5) | | found* | calc.** |
| according to the invention | 20 + 100 | 35 | 0 |

*found = activity found
**calc. = activity calculated using Colby's formula

Examples for the Spray Treatment—Track Sprayer
  Solvent: water
  Adjuvant: rapeseed oil methyl ester
  To produce a suitable solution, 1 part by weight of formulation is mixed with the stated amount of water and adjuvant and the concentrate is diluted with water to the desired concentration.

*Aphis gossypii* Test
  Cotton plants (*Gossypium herbaceum*) which are heavily infested by the cotton aphid (*Aphis gossypii*) are sprayed with the desired concentration of the application solution.

*Heliothis armigera* Test
  Cotton plants (*Gossypium hirsutum*) are sprayed with the desired application concentration and populated with caterpillars of the cotton bollworm (*Heliothis armigera*) while the leaves are still moist.

*Metopolophium dirhodum* Test
  Barley plants (*Hordeum vulgare*) which are heavily infested by a cereal aphid (*Metopolophium dirhodum*) are sprayed with the desired concentration of the application solution.

*Myzus persicae* Test
  Bell pepper plants (*Capsicum sativum*) which are heavily infested by the green peach aphid (*Myzus persicae*) are sprayed with the desired concentration of the application solution.

*Spodoptera frugiperda* Test
  Corn plants (*Zea mais*) are sprayed with the desired application concentration and populated with caterpillars of the armyworm (*Spodoptera frugiperda*) while the leaves are still moist.

After the desired period of time, the kill in % is determined. 100% means that all larvae or aphids have been killed; 0% means that none of the larvae or aphids have been killed. The determined kill rates are entered into Colby's formula (see sheet 1).

In this test, for example, the following combinations according to the present application show a synergistically enhanced activity compared to the components applied on their own:

TABLE G1

Plant-damaging insects
*Aphis gossypii* test

| Formulation | Concentration in g ai/ha | Kill in % after $3^d$ | |
|---|---|---|---|
| I-a-45 WG 50 | 120 | 57 | |
| isoxadifen-ethyl WG 50 | 50 | 0 | |
| I-a-45 + isoxadifen-ethyl (2.4:1) | | found* | calc.** |
| according to the invention | 120 + 50 | 87 | 57 |
| mefenpyr WG 15 | 50 | 0 | |
| I-a-45 + mefenpyr (2.4:1) | | found* | calc.** |
| according to the invention | 120 + 50 | 83 | 57 |
| cloquintocet-mexyl WP 20 | 50 | 0 | |
| I-a-45 + cloquintocet-mexyl (2.4:1) | | found* | calc.** |
| according to the invention | 120 + 50 | 80 | 57 |

*found = activity found
**calc. = activity calculated using Colby's formula

TABLE G2

Plant-damaging insects
*Aphis gossypii* test

| Formulation | Concentration in g ai/ha | Kill in % after $2^d$ | |
|---|---|---|---|
| flonicamid (I-a-2) WG 50 | 120 | 0 | |
| isoxadifen-ethyl WG 50 | 50 | 0 | |
| flonicamid (I-a-2) + isoxadifen-ethyl (2.4:1) | | found* | calc.** |
| according to the invention | 120 + 50 | 50 | 0 |
| mefenpyr WG 15 | 50 | 0 | |
| flonicamid (I-a-2) + mefenpyr (2.4:1) | | found* | calc.** |
| according to the invention | 120 + 50 | 50 | 0 |
| IV-e-5 WG 50 | 50 | 0 | |
| flonicamid (I-a-2) + IV-e-5 (2.4:1) | | found* | calc.** |
| according to the invention | 120 + 50 | 40 | 0 |
| cloquintocet-mexyl WP 20 | 50 | 0 | |
| flonicamid (I-a-2) + cloquintocet-mexyl (2.4:1) | | found* | calc.** |
| according to the invention | 120 + 50 | 60 | 0 |

*found = activity found
**calc. = activity calculated using Colby's formula

TABLE H

Plant-damaging insects
*Heliothis armigera* test

| Formulation | Concentration in g ai/ha | Kill in % after $3^d$ | |
|---|---|---|---|
| III-a-4 SC 015 | 0.192 | 38 | |
| isoxadifen-ethyl WG 50 | 50 | 0 | |
| III-a-4 + isoxadifen-ethyl (1:260.4) | | found* | calc.** |
| according to the invention | 0192 + 50 | 88 | 38 |
| mefenpyr WG 15 | 50 | 0 | |
| III-a-4 + mefenpyr (1:260.4) | | found* | calc.** |
| according to the invention | 0.192 + 50 | 75 | 38 |
| IV-e-5 WG 50 | 50 | 0 | |
| III-a-4 + IV-e-5 (1:260.4) | | found* | calc.** |
| according to the invention | 0.192 + 50 | 100 | 38 |
| cloquintocet-mexyl WP 20 | 50 | 0 | |

TABLE H-continued

Plant-damaging insects
*Heliothis armigera* test

| Formulation | Concentration in g ai/ha | Kill in % after 3$^d$ | |
|---|---|---|---|
| | | found* | calc.** |
| III-a-4 + cloquintocet-mexyl | | | |
| (1:260.4) | | | |
| according to the invention | 0.192 + 50 | 100 | 38 |

*found = activity found
**calc. = activity calculated using Colby's formula

TABLE I1

Plant-damaging insects
*Metopolophium dirhodum* test

| Formulation | Concentration in g ai/ha | Kill in % after 7$^d$ | |
|---|---|---|---|
| I-a-45 WG 50 | 24 | 53 | |
| isoxadifen-ethyl WG 50 | 50 | 0 | |
| I-a-45 + isoxadifen-ethyl (1:2.1) | | found* | calc.** |
| according to the invention | 24 + 50 | 80 | 53 |
| mefenpyr WG 15 | 50 | 0 | |
| I-a-45 + mefenpyr (1:2.1) | | found* | calc.** |
| according to the invention | 24 + 50 | 86 | 53 |
| IV-e-5 a.i. | 50 | 0 | |
| I-a-45 + IV-e-5 (1:2.1) | | found* | calc.** |
| according to the invention | 24 + 50 | 77 | 53 |
| cloquintocet-mexyl WP 20 | 50 | 5 | |
| I-a-45 + cloquintocet-mexyl (1:2.1) | | found* | calc.** |
| according to the invention | 24 + 50 | 99 | 53 |

*found = activity found
**calc. = activity calculated using Colby's formula

TABLE I2

Plant-damaging insects
*Metopolophium dirhodum* test

| Formulation | Concentration in g ai/ha | Kill in % after 7$^d$ | |
|---|---|---|---|
| flonicamid (I-a-2) WG 50 | 4.8 | 70 | |
| isoxadifen-ethyl WG 50 | 50 | 0 | |
| flonicamid (I-a-2) + isoxadifen-ethyl | | found* | calc.** |
| (1:10.42) | | | |
| according to the invention | 4.8 + 50 | 99 | 70 |
| mefenpyr WG 15 | 50 | 0 | |
| flonicamid (I-a-2) + mefenpyr | | found* | calc.** |
| (1:10.42) | | | |
| according to the invention | 4.8 + 50 | 88 | 70 |
| IV-e-5 a.i. | 50 | 0 | |
| flonicamid (I-a-2) + IV-e-5 (1:10.42) | | found* | calc.** |
| according to the invention | 4.8 + 50 | 100 | 70 |
| cloquintocet-mexyl WP 20 | 50 | 5 | |
| flonicamid (I-a-2) + cloquintocet- | | found* | calc.** |
| mexyl (1:10.42) | | | |
| according to the invention | 4.8 + 50 | 90 | 70 |

*found = activity found
**calc. = activity calculated using Colby's formula

TABLE J

Plant-damaging insects
*Myzus persicae* test

| Formulation | Concentration in g ai/ha | Kill in % after 3$^d$ | |
|---|---|---|---|
| I-a-45 WG 50 | 120 | 70 | |
| isoxadifen-ethyl WG 50 | 50 | 0 | |
| I-a-45 + isoxadifen-ethyl (2.4:1) | | found* | calc.** |
| according to the invention | 120 + 50 | 90 | 70 |
| mefenpyr WG 15 | 50 | 0 | |
| I-a-45 + mefenpyr (2.4:1) | | found* | calc.** |
| according to the invention | 120 + 50 | 90 | 70 |
| IV-e-5 WG 50 | 50 | 0 | |
| I-a-45 + IV-e-5 (2.4:1) | | found* | calc.** |
| according to the invention | 120 + 50 | 90 | 70 |
| cloquintocet-mexyl WP 20 | 50 | 0 | |
| I-a-45 + cloquintocet-mexyl (2.4:1) | | found* | calc.** |
| according to the invention | 120 + 50 | 87 | 70 |
| flonicamid (I-a-2) WG 50 | 4.8 | 50 | |
| isoxadifen-ethyl WG 50 | 50 | 0 | |
| flonicamid (I-a-2) + isoxadifen-ethyl | | found* | calc.** |
| (1:10.42) | | | |
| according to the invention | 4.8 + 50 | 80 | 50 |

*found = activity found
**calc. = activity calculated using Colby's formula

TABLE K

Plant-damaging insects
*Spodoptera frugiperda* test

| Formulation | Concentration in g ai/ha | Kill in % after 7$^d$ | |
|---|---|---|---|
| III-a-4 SC 015 | 0.192 | 60 | |
| isoxadifen-ethyl WG 50 | 50 | 0 | |
| III-a-4 + isoxadifen-ethyl (1:260.4) | | found* | calc.** |
| according to the invention | 0.192 + 50 | 100 | 60 |
| mefenpyr WG 15 | 50 | 0 | |
| III-a-4 + mefenpyr (1:260.4) | | found* | calc.** |
| according to the invention | 0.192 + 50 | 100 | 60 |
| IV-e-5 WG 50 | 50 | 0 | |
| III-a-4 + III-e-5 (1:260.4) | | found* | calc.** |
| according to the invention | 0.192 + 50 | 100 | 60 |

*found = activity found
**calc. = activity calculated using Colby's formula

The invention claimed is:

1. A synergistic insecticide or acaricide composition, comprising an effective amount of a compound of the formula III-a-18:

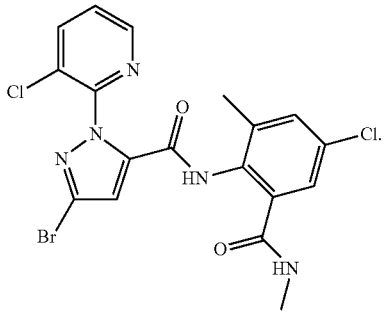

III-a-4 and at least one crop plant compatibility-improving compound is selected from the group consisting of cloquintocet-mexyl, isoxadifen-ethyl, mefenpyr-diethyl, dichlormid, furilazole, fenclorim, and the compound IV-e-5 below:

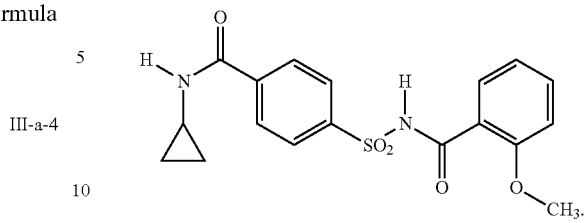

(IV-e-5)

2. The composition according to claim 1, further comprising extenders, emulsifiers, dispersants, or foam formers.

3. A method of controlling insects or acarids, comprising applying to said insects, acarids and/or their habitat an effective amount of the composition according to claim 1.

4. The Composition according to claim 1, wherein said at least one crop plant compatibility-improving compound is selected from the group consisting of cloquintocet-mexyl, isoxadifen-ethyl, mefenpyr-diethyl and the compound IV-e-5.

5. The composition according to claim 4, further comprising extenders, emulsifiers, dispersants, or foam formers.

6. A method of controlling, insects or acarids, comprising, applying to said insects, acarids and/or their habitat an effective amount of the composition according to claim 4.

* * * * *